United States Patent [19]

Zoller et al.

[11] Patent Number: 4,816,454

[45] Date of Patent: Mar. 28, 1989

[54] 4,5-DIHYDRO-3(2H)-PYRIDAZINONES AND THEIR PHARMACOLOGICAL USE

[75] Inventors: Gerhard Zoller, Maintal; Rudi Beyerle, Frankfurt; Melitta Just; Helmut Bohn, both of Schöneck; Piero Martorana, Bad Homburg; Rolf-Eberhard Nitz, Frankfurt, all of Fed. Rep. of Germany

[73] Assignee: Cassella Aktiengesellschaft, Frankfurt am Main, Fed. Rep. of Germany

[21] Appl. No.: 775,420

[22] Filed: Sep. 12, 1985

[30] Foreign Application Priority Data

Sep. 21, 1984 [DE] Fed. Rep. of Germany ....... 3434680
Jun. 21, 1985 [DE] Fed. Rep. of Germany ....... 3522193

[51] Int. Cl.$^4$ .................. A61K 31/535; C07D 413/04
[52] U.S. Cl. ............................... 514/211; 514/226.8; 514/227.8; 514/230.5; 514/247; 514/252; 514/253; 540/488; 544/54; 544/58.2; 544/58.4; 544/58.6; 544/92; 544/238; 544/239
[58] Field of Search .................. 540/488; 544/92, 238, 544/239, 54, 58.2, 58.4, 58.6; 514/211, 222, 226, 228, 230, 232, 234, 235, 247, 252, 253, 230.5, 227.8, 226.8

[56] References Cited

U.S. PATENT DOCUMENTS

| | | | |
|---|---|---|---|
| 4,360,672 | 11/1982 | Parg et al. | 544/238 X |
| 4,361,563 | 11/1982 | Austel et al. | 544/238 X |
| 4,404,203 | 9/1983 | Sircar | 544/239 X |
| 4,551,455 | 11/1985 | Hilboll et al. | 544/238 X |
| 4,666,902 | 5/1987 | Zoller et al. | 514/212 |

FOREIGN PATENT DOCUMENTS 155798 9/1985 European Pat. Off. .
167995 1/1986 European Pat. Off. .
3302021 7/1984 Fed. Rep. of Germany .
1404022 8/1975 United Kingdom .

Primary Examiner—Richard L. Raymond

[57] ABSTRACT

Substituted 4,5-dihydro-3(2H)-pyridazinones of the formula I

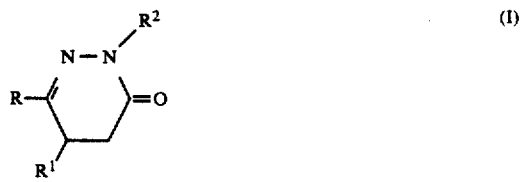

wherein R, for example, denotes a radical of the formula

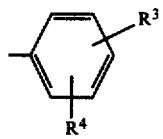

$R^1$ and $R^2$, for example, denote hydrogen or methyl, $R^3$, for example, denotes 2-methoxy-ethoxy, 3-pyridyl-methoxy, amino-carbonyl-methoxy, hydroxy-carbonyl-methoxy, methyl-thio, (2-methoxy-ethyl)-amino-carbonyl-methoxy, 3-pyridyl-methyl or 5-methyl-1,3,4-oxadiazol-2-yl and $R^4$, for example, denotes hydrogen, have useful pharmacological properties and can therefore be used for the preparation of pharmacological products.

21 Claims, No Drawings

4,5-DIHYDRO-3(2H)-PYRIDAZINONES AND THEIR PHARMACOLOGICAL USE

The present invention relates to substituted 4,5-dihydro-3(2H)-pyridazinones of the formula I

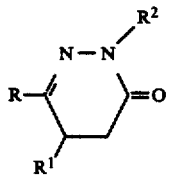

wherein R denotes a radical of the formula

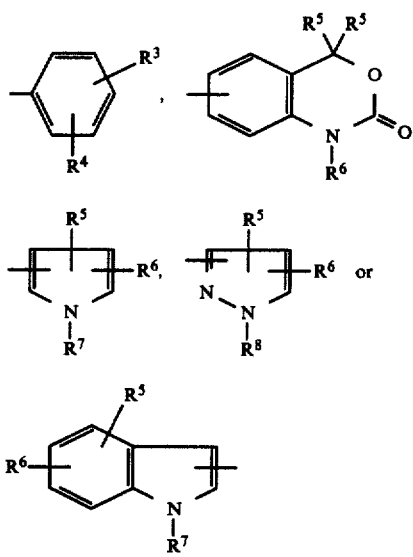

$R^1$ and $R^2$ independently of one another denote hydrogen or unsubstituted straight chain or branched chain alkyl, $R^3$ denotes alkoxy-alkoxy, amino-carbonyl-alkoxy, alkoxy-alkylamino-carbonyl-alkoxy, hydroxyalkylamino, non-urea thiazolidinyl-carbonylamino, monoalkylamino-carbonyl-alkoxy, alkoxy-carbonyl-alkoxy, hydroxy-carbonyl-alkoxy, alkyl-thio, alkyl-sulphinyl, alkylsulphonyl, 2-oxo-pyrrolidinyl, 2-oxo-piperidinyl, 2,5-dioxo-piperidinyl, 2,5-dioxo-pyrrolidinyl, 2-oxo-imidazolidinyl, 2-oxo-hexahydropyrimidinyl, 2,4-dioxo-imidazolidinyl, 2,4-dioxo-hexahydro-pyrimidinyl, 2-oxo-1,3-oxazolidinyl, 3-oxo-pyrazolidinyl, (2-($R^9$-carbonyl)-pyrrolidinyl-alkoxy, alkyl-substituted or alkoxy-, substituted by pyridyl, imidazolyl, oxadiazolyl, oxo-pyranyl, 2-hydroxy-pyridinyl, pyrrolinyl or oxo-oxazolidinyl, it being possible for the oxopyranyl, oxo-oxazolidinyl and oxadiazolyl in turn to be substituted by alkyl or alkoxycarbonyl, or denotes a radical of the formula $R^{10}$—CO—NH—, $R^4$ denotes hydrogen, alkyl, alkoxy, hydroxyl, alkanoyloxy or halogen, $R^5$, $R^6$ and $R^7$ independently of one another denote hydrogen, alkyl, alkoxy, hydroxy, halogen, amino, monoalkylamino or dialkylamino, $R^8$ denotes hydrogen, alkyl or phenyl, $R^9$ denotes hydroxyl, alkoxy, amino, monoalkylamino or dialkylamino, $R^{10}$ denotes p-chloro-phenoxymethyl, 2,4-dioxo-imidazolidin-5-yl-methyl, 2,4-dioxo-imidazoldiin-3-yl-methyl, 3-pyridyl-oxymethyl, 3-pyridyl-methoxy-methyl, 4-pyridyl-thiomethyl, 4-pyridyl-sulphinyl-methyl, 4-pyridyl-sulphonyl-methyl, 2-oxothiazolidin-4-yl, 3-oxo-perhydro-1,4-thiazin-5-yl, 1-oxido-3-oxo-perhydro-1,4-thiazin-5-yl, 5-oxo-perhydro-1,4-thiazepin-3-yl, 1-oxido-5-oxo-perhydro-1,4-thiazepin-3-yl, 1,1-dioxido-5-oxo-perhydro-1,4-thiazepin-3-yl, or a heterocyclic radical containing both sulfur and nitrogen in the ring and having the carbonyl group attached to a ring carbon as a non-urea linkage, such as of the formula

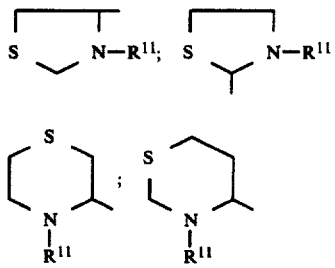

$R^{11}$ denotes hydrogen or a radical of the formula $$R^{12}-CO-$$

and $R^{12}$ denotes hydrogen, alkyl with 1 to 5 C atoms, alkoxy with 1 to 5 C atoms, benzyl or benzyloxy, and their pharmacologically acceptable addition salts.

The invention also relates to processes for the preparation of the compounds of the formula I and their use as pharmacological products.

The alkyl and/or alkoxy radicals $R^1$ to $R^{12}$, including those in combination with one another or those occurring as substituents or mutual substituents, can be straight-chain or branched. As a rule, they have 1 to 4 C atoms.

The halogen $R^4$, $R^5$, $R^6$ and $R^7$ denotes, in particular, bromine or chlorine.

The alkanoyloxy radical $R^4$ as a rule has 1 to 5 C atoms and represents, for example, formyloxy, acetoxy, butyryloxy, isobutyryloxy, valeryloxy or isovaleryloxy.

$R^1$ and $R^2$ independently of one another preferably denote hydrogen and/or methyl. Particularly preferably, $R^1$ represents methyl and $R^2$ represents hydrogen.

Preferred radicals R are: the phenyl radical substituted by $R^3$ and $R^4$, in particular the phenyl radical substituted by $R^3$ in the 4-position, pyrrolyl, in particular 2-pyrrolyl, indolyl, in particular 3-indolyl, 5-amino-1,3-dimethyl-pyrazol-4-yl, 5-hydroxy-3-methyl-1-phenyl-pyrazol-4-yl and 1,4-dihydro-2-oxo-benz(d)(1,3)-oxazinyl, in particular 1,4-dihydro-2-oxo-benz(d)(1,3)-oxazin-6-yl. The radical

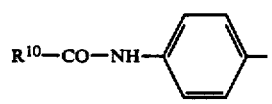

is furthermore preferred for R.

$R^4$ is preferably hydrogen, $(C_1-C_4)$alkyl or $(C_1-C_4)$alkoxy. $R^4$ is, in particular, hydrogen or methoxy, and especially preferably hydrogen.

$R^3$ is preferably: 2-methoxy-ethoxy, 3-pyridinyl-methoxy, amino-carbonyl-methoxy, hydroxy-carbonyl-methoxy, methylthio, (2-methoxy-ethyl)-amino-carbonyl-methoxy, 3-pyridyl-methyl, 5-methyl-1,3,4-oxadiazol-2-yl, 2-hydroxy-4-methyl-pyrid-6-ylmethoxy, 2-(imidazol-1-yl)-ethoxy, (2-oxo-oxazolidin-5-yl)-methoxy, 2-(2-oxo-pyrrolidin-1-yl)-ethyl-amino-carbonyl-amino, 2-(methoxycarbonyl-pyrrolidin-1-yl)-ethoxy, 2-oxo-pyrrolidin-1-yl, 2,5-dioxo-pyrrolidin-1-yl, 2-oxo-imidazoldiin-1-yl, 3-oxo-pyrazolidin-1-yl, 2,4-dioxo-imidazolidin-1-yl, 2-oxo-oxazolidin-3-yl or thiazolidin-4-yl-carbonyl-amino. $R^3$ is furthermore preferably a radical of the formula $R^{10}$—CO—NH—.

Examples of the radical $R^{11}$ are: hydrogen, formyl, acetyl, propionyl, butyryl, isobutyryl, valeryl, isovaleryl, pivaloyl, phenylacetyl, methoxy-carbonyl, ethoxy-carbonyl, propoxy-carbonyl, isopropoxy-carbonyl, butoxy-carbonyl, isobutoxy-carbonyl, tert.-butoxy-carbonyl and benzyloxy-carbonyl. Hydrogen, formyl, acetyl, tert.-butoxy-carbonyl and benzyloxy-carbonyl are preferred for the radical $R^{11}$.

Preferred compounds of the formula I have one or, preferably, several preferred radicals for R to $R^{12}$. The compounds of the formula I can exist in tautomeric forms if the conditions for these exist.

Preferred compounds are also substituted 4,5-dihydro-3(2H)-pyridazinones of the formula Ia

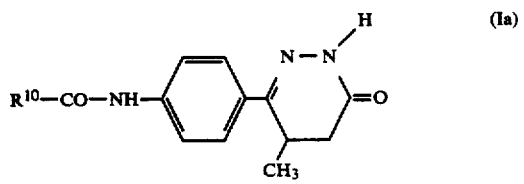

(Ia)

wherein $R^{10}$ has the meaning already given.

The compounds of the formula I can be prepared by a process analogous to the preparation of other 4,5-dihydroo-3(2H)-pyridazinones, in which a carboxylic acid or a carboxylic acid derivative of the formula II is reacted with an N-$R^2$-hydrazine of the formula III in accordance with the following equation:

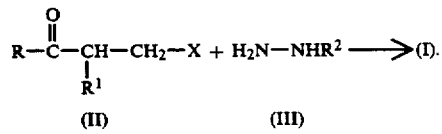

In the formulae II and III, R, $R^1$ and $R^2$ have the meanings already given. In formula II, X denotes —COOH, —COCl, —CO—O—CO—$R^{13}$, —CO—O$R^{13}$ or —CN, wherein $R^{13}$ denotes an organic radical, in particular an alkyl radical, preferably an alkyl radical with 1 to 4 C atoms, and especially preferably methyl.

If $R^2$=H, the compound of the formula III is hydrazine itself. If $R^2$=alkyl, the compound of the formula III is an asymmetrically alkylated hydrazine. The compound of the formula III can also be employed in the form of its hydrate. The reaction between the compounds II and III is advantageously carried out in the liquid phase, the presence of an inert solvent or diluent as a rule being necessary.

Examples of suitable solvents or diluents are alcohols, in particular those with 1 to 6 C atoms, such as, for example, methanol, ethanol, i- and n-propanol, i-, sec.- and tert.-butanol, n-, i-, sec.- and tert.-pentanol, n-hexanol, cyclopentanol and cyclohexanol; ethers, in particular those with 2 to 8 C atoms in the molecule, such as, for example, diethyl ether, methyl ethyl ether, di-n-propyl ether, di-isopropyl ether, methyl n-butyl ether, ethyl propyl ether, di-butyl ether, tetrahydrofuran, 1,4-dioxane, 1,2-dimethoxyethane and bis-β-methoxyethyl ether; polyethers, such as, for example, polyethylene glycols with a molecular weight up to about 600; oligoethylene glycol dimethyl ethers, such as, for example, pentaglyme; crown ethers, that is to say cyclic polymers of ethylene glycol of the formula (—O$CH_2CH_2$)$_p$, wherein p is a number, for example, from 4 to 10, and it also being possible for one or more benzene rings to be fused onto the ring; aza- and thia-crown ethers (coronand amines and coronand sulphides); glycols and partially etherified glycols, such as, for example, ethylene glycol, propylene glycol, trimethylene glycol, ethylene glycol monomethyl ether, ethylene glycol monoethyl ether and diethylene glycol monoethyl ether; aliphatic hydrocarbons, such as, for example, benzines and low-boiling and high-boiling petroleum ethers; aromatic hydrocarbons, such as, for example, benzene, toluene and o-, m- and p-xylene; pyridine; halogenated aliphatic or aromatic hydrocarbons, such as, for example, methylene chloride, chloroform, carbon tetrachloride, ethylene chloride, chlorobenzene and dichlorobenzene; nitriles, such as, for example, acetonitrile; amides, such as, for example, dimethylformamide and N-methyl-pyrrolidone; sulphoxides, such as, for example, dimethyl-sulphoxide; and water. Mixtures of various solvents or diluents can also be used.

The reaction between the compounds II and III can in principle be carried out at temperatures between room temperature and the boiling point of the solvent or diluent used.

The compounds of the formula III are known or can be synthesised by processes known for the preparation of N-alkylhydrazines. The compounds of the formula II can be prepared by various processes which are known per se, thus, for example, by acylation of the compounds R—H with $R^2$-maleic acid anhydride and subsequent hydrogenation of the resulting unsaturated compound, for example by the process described in J. Med. Chem. 17, 273 et seq., (1974), and furthermore by Mannich reaction of ketones of the formula R—CO—$CH_2$—$R^1$ with formaldehyde/dimethylamine to give Mannich bases R—CO—CH($R^1$)—$CH_2$—N($CH_3$)$_2$ and subsequent replacement of the amine radical, for example by cyano via the quaternary iodine compound, compounds R—CO—CH($R^1$)—$CH_2$—CN, and if desired compounds R—CO—CH($R^1$)—$CH_2$—COOH therefrom by hydrolysis, being obtained. This reaction sequence is described, for example, in J. Org. Chem. 38, 4044 et seq. (1973). The compounds of the formula II where X=CN can also be prepared, for example, by acylation of compounds of the formula R—H with 2-$R^1$-3-chloropropionic acid chloride in accordance with German Offenlegungsschrift No. 3,328,286, compounds of the formula R—CO—CH($R^1$)—$CH_2$—Cl initially being formed, and the chlorine on these compounds being replaced by CN using NaCN or KCN.

Compounds of the formula II where X=CN give the compounds of the formula I directly when the reaction with the compounds of the formula III is carried out in an aqueous medium or in the presence of water. If the reaction is carried out in an anhydrous medium, the ketimines of the compounds of the formula I are initially formed, and these are then hydrolysed in a manner which is known per se to give the compounds of the formula I.

Starting compounds of the formula II where X=CN can easily be converted into starting compounds of the formula II with different meanings of X by processes which are known per se.

Starting compounds of the formula II where $R^1$=—$CH_3$ and X=—CO—$OR^{13}$, preferably where $R^{13}$=—$CH_3$, can be prepared in a particularly simple manner and in a high yield by a process in which compounds of the formula R—H are acylated with 3-($R^8O$-carbonyl)-isobutyryl chloride (=$R^{13}O$—CO—$CH_2$—CH($CH_3$)—CO—Cl) under the conditions of Friedel-Crafts ketone synthesis. Acylation with 3-($R^{13}O$-carbonyl)-isobutyryl chloride is widely applicable, so that, according to the reaction:

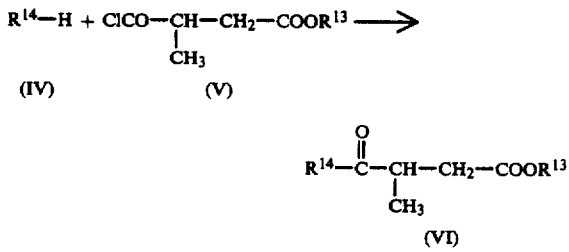

wherein $R^{14}$ denotes R or an aromatic or heteroaromatic hydrocarbon radical, which can also be monosubstituted or polysubstituted, and $R^{13}$ denotes the radicals already mentioned, preferably alkyl with 1 to 4 C atoms and especially preferably methyl, ketocarboxylic acid esters of the formula VI can be prepared in a simple manner in high yields starting from aromatic or heteroaromatic hydrocarbon radicals of the formula IV, in particular compounds of the formula R—H, wherein R has the meaning already mentioned above, by reaction with the compounds of the formula V.

Besides the radical R already mentioned, $R^{14}$ can be, for example: phenyl, naphthyl or phenyl or naphthyl which is monosubstituted or polysubstituted by ($C_1$–$C_5$)alkyl, halogen, ($C_1$–$C_5$)alkyl-carbonyl-amino, ($C_1$–$C_4$)alkoxy-carbonyl, ($C_1$–$C_5$)alkoxy and/or cyano.

Examples of suitable starting compounds of the formula IV are: benzene, monoalkylbenzenes, such as, for example, toluene and ethylbenzene, dialkylbenzenes, such as, for example, o-, m- and p-xylene, pseudocumene, mesitol, prehnitol, isodurene, durene, pentamethylbenzene, p-dibutylbenzene, p-diisopropylbenzene, indane, tetralin, diphenylmethane, 1,2-diphenylethane, chlorobenzene, bromobenzene, o-bromo-toluene, o-, m- and p-chloro-toluene m-xylenol, phenol, diphenyl ether, dimethylaniline, naphthalene, 1-alkyl-naphthalenes, such as 1-methyl-naphthalene, 2-bromonaphthalene, anthracene, phenanthrene, furan, pyrone, chromane, phenol ethers, such as, for example, anisole, phenetole and 1,2-dimethoxybenzene, phenyl-imidazoles, such as, for example, 1-phenyl-imidazole, phenyl-pyridines, such as, for example, 3-phenylpyridine, 2- or 3-phenyl-thiophene, benzimidazole, 2-alkylbenzimidazoles, in particular 2-($C_1$–$C_4$)alkyl-benzimidazole, N-acyl-anilines, such as, for example, acetanilide, N-acyl-N-alkylanilines, such as, for example, N-methyl-acetanilide, N-alkyl-indolin-2-ones, in particular N-($C_1$–$C_4$)alkyl-indolin-2-ones, N-alkyl-1,2,3,4-tetrahydro-2-oxoquinolines, in particular N-($C_1$–$C_4$)alkyl-1,2,3,4-tetrahydro-2-oxo-quinolines, coumaran, N-acyl-1,2,3,4-tetrahydro-4-oxo-quinolines, such as, for example, N-acetyl- or -propionyl-1,2,3,4-tetrahydro-4-oxo-quinoline, N-acyl-indolines, such as, for example, N-acetyl-indoline, imidazolylalkyl-benzenes, pyridyl-alkyl-benzenes, thienyl-alkyl-benzenes and furyl-alkyl-benzenes, the alkyl radicals in the abovementioned compounds having, in particular, 1 to 4 C atoms.

The starting compounds of the formula V required can easily be synthesised by a process analogous to the preparation of 3-carbomethoxy-isobutyryl chloride, which is known (compare J. Org. Chem. 17, 122 (1952)), in which itaconic anhydride is reacted with an alcohol $R^{13}OH$ to give a $\beta$-$R^{13}$ hydrogen-itaconate, this is then hydrogenated on the C—C double bond to give a $\beta$-$R^{13}$ hydrogen-succinate and this is then converted into the starting compound of the formula V with, for example, thionyl chloride.

The reaction of the compounds IV with the compounds V is carried out in a suitable inert solvent in the presence of a suitable Friedel-Crafts catalyst at temperatures from −30° C. up to the boiling point of the solvent used, temperatures between 0° C. and 25° C. usually being most appropriate.

Suitable solvents are all the solvents used in Friedel-Crafts acylation, such as, for example, nitrobenzene, carbon disulphide, 1,2-dichloroethane, ethylene chloride, 1,2-dichlorobenzene, methylene chloride, dimethylformamide and the like.

Suitable Friedel-Crafts catalysts are Lewis acids, such as, for example, metal halides, thus, for example, $AlCl_3$, $AlBr_3$, $FeCl_3$, $FeBr_3$, $SbCl_5$, $SbBr_3$, $TiCl_4$, $BiCl_3$, $ZnCl_4$, $ZnCl_2$ and $SnCl_2$, and furthermore boron compounds, such as $BF_3$ or $BBr_3$, and also $PCl_5$ or $POCl_3$.

As is customary with Friedel-Crafts acylations, the reaction is carried out with the exclusion of moisture and the catalyst is as a rule employed in 1 to 4 times the molar amount, based on the acid chloride of the formula V. The reaction and working up are otherwise carried out in the manner customary for Friedel-Crafts acylations.

Compounds of the formula I in which $R^2$ denotes an alkyl radical can also be prepared from compounds of the formula I in which $R^1$ denotes hydrogen by reaction in a manner which is known per se with an alkylating agent which introduces the alkyl radical $R^2$. The alkylation is advantageously carried out in a suitable solvent at temperatures from room temperature up to the reflux temperature of the solvent. Examples of possible alkylating agents are alkyl halides, dialkyl sulphates or alkyl tosylates, through which the alkyl radical $R^2$ is introduced.

The compounds of the formula Ia can be prepared by a process analogous to the preparation of other carboxylic acid amides by acylation of 6-(4-aminophenyl)-4,5-dihydro-5-methyl-3(2H)-pyridazinone of the formula VII

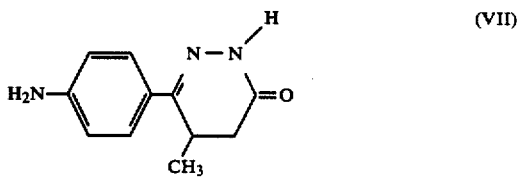

with acylating agents which introduce the acyl radical $R^{10}$—CO—. In this acylation, one hydrogen atom of the amino group of the compound II is replaced by the radical $R^{10}$—CO—. Examples of suitable acylating agents are compounds of the formula VIII $$R^{10}-CO-Y \qquad (VIII)$$

wherein $R^{10}$ has the meaning already given and Y=-halogen, in particular —Cl or —Br, —OH, —O—alkyl, in particular with 1 to 5 C atoms, —O—CO—$R^{10}$ or —O—CO—O—alkyl, in particular with 1 to 5 C atoms in the alkyl radical, —O—aryl, —O—nitroaryl or —O—dinitroaryl, in particular phenoxy, 2- or 4-nitrophenoxy or 2,4-dinitrophenoxy, —OCH$_2$CN or the radical of an azole or benzazole, bonded via an N atom, with at least 2N atoms in the quasi-aromatic five-membered ring.

The acylating agents of the formula VIII are thus, for example, carboxylic acid halides, in particular carboxylic acid chlorides and carboxylic acid bromides, of which the carboxylic acid chlorides are preferred, carboxylic acids, carboxylic acid esters, carboxylic acid anhydrides or mixed carboxylic acid carbonic acid anhydrides or heterocyclic amides or azolides.

It is not absolutely essential for the acylating agents of the formula VIII wherein Y has the meaning given, with the exception of —OH, to be employed in a pure form in the acylation, but they can also be produced in situ from the carboxylic acids of the formula VIIIa $$R^{10}-CO-OH \qquad (VIIIa)$$

shortly before the acylation reaction or during the acylation reaction. That is to say, the carboxylic acids of the formula VIIIa can also be used as the acylating agent.

If the carboxylic acids of the formula VIIIa are used as the acylating agent, it is advantageous to add an activating agent, which has the object of increasing the acylating potential of the carboxylic acid or of activating the acid. Examples of suitable activating agents of this type are:
 (a) dehydrating or water-bonding agents and
 (b) agents which are capable of converting the carboxylic acids of the formula VIIIa into the corresponding acid halides, anhydrides, esters, mixed carboxylic acid/carbonic acid anhydrides or azolides which act as acylating agents.

Examples of suitable water-bonding or dehydrating agents are N,N'-disubstituted carbo-diimides of the formula IX $$R'-N=C=N-R'' \qquad (IX)$$

especially if the radical R' and, if appropriate, also the radical R" is a secondary or tertiary alkyl radical (compare Methodicum Chimicum, Verlag G. Thieme Stuttgart, Volume 6, (1974) page 682). Examples of suitable carbo-diimides are di-isopropyl-, di-cyclohexyl- or methyl-tert.-butyl-carbo-diimide. In carrying out the acylation reaction, the compound of the formula VII, the carboxylic acid of the formula VIIIa and the carbodiimide are then brought together in a suitable inert solvent or diluent, the desired acylation product of the formula Ia and, from the carbodiimide, the corresponding disubstituted urea being formed.

Examples of agents which can convert the carboxylic acids of the formula VIIIa into the corresponding halides, carboxylic acid esters, anhydrides, mixed carboxylic acid/carbonic acid anhydrides or azolides are, above all, carbonic acid derivatives, such as, for example, phosgene Cl—CO—Cl, chloroformic acid esters Cl—CO—O—alkyl, in particular with 1 to 5 C atoms in the alkyl radical (compare, for example, Tetrahedron Letters 24 (1983) 3365), carbonic acid esters R''''—O—CO—O—R'''', such as, for example, N,N'-disuccinimido-carbonate, diphthalimido-carbonate, 1,1'-(carbonyldioxy)-dibenzo-triazole or di-2-pyridyl carbonate (compare, for example, Tetrahedron Letters, Volume 25, No. 43, 4943–4946), if appropriate in the presence of suitable catalysts, such as, for example, 4-dimethylaminopyridine, or heterocyclic diamides of the carbonic acid of the formula A—CO—A, wherein A denotes a radical of an azole, bonded via an N atom, with at least 2 nitrogen atoms in the quasi-aromatic five-membered ring. Examples of suitable heterocyclic diamides of this type are N,N'-carbonyl-diimidazole, 2,2'-carbonyl-di-1,2,3-triazole, 1,1'-carbonyl-di-1,2,4-triazole, N,N'-carbonyl-dipyrazole, 2,2'-carbonyl-ditetrazole, N,N'-carbonyl-benzylimidazole or N,N'-carbonylbenzotriazole. These compounds are in general combined with the carboxylic acid of the formula VIIIa, before the actual acylation of the compound VII, in a suitable solvent or dispersing agent in stoichiometric proportions at temperatures from 0° C. up to the boiling point of the solvent or diluent, usually at 10° to 100° C., preferably 20° to 80° C., the azolide of the formula $$R^{10}-CO-A$$

wherein $R^{10}$ and A have the meanings already given, which acts as the actual acylating agent, being formed in a few minutes. This azolide can then be used immediately in the same pot for acylation of the amine of the formula VII (compare, for example, H. A. Staab, M. Lücking and F. H. Dürr, Chem. Ber. 95, (1962), 1275, and H. A. Staab and W. Rohr "Synthesen mit heterocyclischen Amiden (Azoliden)" ("Syntheses with heterocyclic amides (azolides)") in "Neuere Methoden der Präparativen Organischen Chemie" ("Recent methods of preparative organic chemistry"), Volume V, Verlag Chemie, 1967, page 53 et seq., in particular page 68). The commercially available N,N'-carbonyl-diimidazole is frequently used as the N,N'-carbonyl-diazole. However, the other N,N'-carbonylazoles are also easily accessible from the particular azole and phosgene.

Instead of the carbonic acid derivatives, the corresponding derivatives of oxalic acid, such as, for example, oxalyl chloride Cl—CO—CO—Cl (compare, for example, British Patent Specification No. 2,139,725) or N,N-oxalyl-diazoles A—CO—CO—A, wherein A has the meaning already given (compare, for example, Bull. Chem. Soc. Jap. 57, 3597–3598 (1984)), can frequently also be used as activating agents for the carboxylic acids of the formula VIIIa.

However, other compounds, such as, for example, methylethylphosphinic anhydride (compare, for example, German Offenlegungsschrift No. 3,101,427) are also suitable as activating agents for the carboxylic acids VIIIa.

The reaction between the acylating agent and the compound VII is advantageously carried out in the liquid phase in the presence of an inert solvent or diluent.

Examples of suitable solvents or diluents are those which have already been mentioned as solvents or diluents for the reaction between the compounds II and III.

The alcohols, glycols and partially etherified glycols mentioned there as solvents or diluents and water are usually suitable only for acylation with carboxylic acid esters, whilst they are not sufficiently inert and are therefore less suitable for carrying out the acylation with other acylating agents, because of the competing formation of esters, glycol esters or acids.

The molar ratio between the compound of the formula VII and the acylating agent of the formula VIII is 1:1. The acylating agent is advantageously employed in a slight molar excess. Excesses of up to 30 ml % are as a rule sufficient, that is to say the molar ratio between the compound of the formula VII and the acylating agent of the formula VII is usually 1:(1 to 1.3), preferably 1:(1 to 1.2). If an acid is split off during the acylation reaction, it is advantageous to add an acid-trapping agent, such as, for example, an alkali metal hydroxide, such as, for example, sodium hydroxide, potassium hydroxide or lithium hydroxide, or a tertiary organic amine, such as, for example, pyridine or triethylamine. Suitable catalysts, such as, for example, 4-dimethylaminopyridine, can also be added for the acylation reaction.

The reaction between the acylating agent of the formula VIII and the compound VII can in principle be carried out at temperatures between $-10°$ C. and the boiling point of the solvent or diluent used. In many cases, the reaction is carried out at $0°$ to $50°$ C., in particular at $10°$ to $30°$ C. and preferably at room temperature.

To prepare compounds of the formula Ia according to the invention in which $R^{11}$ denotes hydrogen, it may be advantageous first to prepare a compound of te formula Ia in which $R^{11}$ denotes a radical of the formula $R^{12}$—CO—, and then to replace this radical by hydrogen in a manner which is known per se, for example by hydrogenation or reaction with acids or bases.

If the carboxylic acid derivatives employed as the acylating agent have a centre of asymmetry, diastereomeric amides are obtained by reaction with compounds of the formula VII. Both the enantiomerically pure carboxylic acids and the racemates have been used. Compounds according to the invention are the resulting diastereomer mixtures or diastereomerically pure amides which can be prepared by recrystallisation of the amides obtained using enantiomerically pure carboxylic acid derivatives.

If the compounds of the formula I contain basic radicals, they form acid addition salts with acids. Inorganic and organic acids are suitable for the formation of such acid addition salts. Examples of suitable acids are: hydrogen chloride, hydrogen bromide, naphthalenedisulphonic acids, in particular 1,5-naphthalenedisulphonic acid, phosphoric acid, nitric acid, sulphuric acid, oxalic acid, lactic acid, tartaric acid, acetic acid, salicylic acid, benzoic acid, formic acid, propionic acid, pivalic acid, diethylacetic acid, malonic acid, succinic acid, pimelic acid, fumaric acid, maleic acid, malic acid, sulphamic acid, phenylpropionic acid, gluconic acid, ascorbic acid, isonicotinic acid, methanesulphonic acid, p-toluenesulphonic acid, citric acid or adipic acid. Pharmacologically acceptable acid addition salts are preferred. The acid addition salts can be prepared in the customary manner by combining the components, advantageously in a suitable solvent or diluent.

Advantageously, for this purpose, the compound of the formula I is dissolved in an organic solvent and a solution of the desired acid is added. Thus, for example, the hydrochlorides of the pyridazinones of the formula I according to the invention can be obtained by dissolving the compound I in alcohol and adding an equivalent amount of a solution of hydrogen chloride in diethyl ether to the alcoholic solution.

The 4,5-dihydro-3(2H)-pyridazinone derivatives of the formula I according to the invention and their pharmacologically acceptable salts exhibit pronounced antithrombotic, platelet aggregation-inhibiting, antianginal, cardiotonic and hypotensive actions. Surprisingly, they are considerably superior to the previously known compounds of the same type of action and are therefore outstandingly suitable for humans for the treatment and prevention of diseases of the heart and the circulatory system, including thromboembolic diseases. They exhibit an excellent activity in various tests, such as, for example, platelet aggregation according to Born, Nature 194, page 927, (1961); arachidonic acid lethality in rabbits, Science 193, page 1085, (1974); and prevention of arterial and venous thromboses in rabbits, and a favourable haemodynamic profile in dogs. Investigation in the tests mentioned and in a number of other tests shows that the compounds which can be prepared according to the invention, surprisingly, have a particularly advantageous action profile which does not exist in this form with known products, coupled with a low toxicity.

The 4,5-dihydro-3(2H)-pyridazinones of the formula I according to the invention and their pharmacologically acceptable acid addition salts can therefore be administered to humans as medicines by themselves, as mixtures with one another or in the form of pharmaceutical formulations which allow enteral or parenteral administration and which contain, as the active constituent, an effective dose of at least one compound of the formula I or of an acid addition salt thereof, in addition to customary pharmaceutically acceptable excipients and additives.

The medicines can be administered orally, for example in the form of pills, tablets, lacquered tablets, coated tablets, hard and soft gelatine capsultes, granules, solutions, syrups, elixirs, emulsions or suspensions or aerosol mixtures. Administration can also be, however, rectal, for example in the form of suppositories, parenteral, for example in the form of injection solutions, or percutaneous, for example in the form of ointments or tinctures.

The pharmaceutical products are prepared in a manner which is known per se, for example by extending the active compounds with pharmaceutically acceptable inorganic and/or organic excipients and/or solvents. The pharmaceutical products can also contain two or more compounds of the formula I or their pharmacologically acceptable acid addition salts. The pharmaceutical products usually contain the therapeutically active compounds or the mixture of therapeutically active compounds in a concentration of about 0.5 to 90% by weight of the total mixture.

Examples of excipients which can be used for the preparation of pills, tablets, coated tablets, hard and soft gelatine capsules or granules are natural rock powders, such as, for example, taclc, aluminas, kaolins and chalk, synthetic rock powders, such as, for example, silicates and silicic acid, sugars, such as, for example, invert sugar, glucose, lactose, maltose, fructose or sucrose, and starch or starch derivatives, such as, for example, maize starch, potato starch or gelatine. Examples of suitable excipients for soft gelatine capsules and suppositories are fats, waxes and paraffins, such as, for example, petroleum oil fractions, natural oils, such as, for example, groundnut oil or sesame oil, hardened oils, semi-solid and liquid polyols and the like. Examples of suitable excipients for the preparation of solutions and syrups are water, alcohols, sucrose, invert sugar, glucose, polyols and the like. Examples of suitable excipients for the preparation of injection solutions are water, alcohols, glycols, glycerol, polyols, vegetable oils and the like.

In addition to the active compounds and excipients, the pharmaceutical products can also contain, in a known manner, additives, such as, for example, fillers, extenders, disintegrating agents, binders, lubricants, wetting agents, stabilisers, emulsifiers, dispersing agents, preservatives, sweeteners, colorants, flavouring or aromatising agents, thickeners, diluents, adjuvants and buffer substances, and furthermore solvent, auxiliary solvents or solubilising agents or agents to achieve a depot effect, as well as salts for modifying the osmotic pressure, coating agents or antioxidants.

The daily dosage can vary within wide limits, for example from 0.001 mg/kg of body weight up to 20 mg/kg of body weight, and should be adapted to suit the individual circumstances in each particular area.

Depending on the mode of administration, the dose is varied within the dosage range mentioned in order to take account of different absorption conditions in a known manner. Thus, in the case of intravenous administration, a dosage more within the lower part of the dosage range mentioned is chosen. In general, daily amounts of about 0.001 to 1 mg/kg, preferably about 0.01 to 0.5 mg/kg of body weight will be administered to achieve effective results in the case of intravenous administration. In the case of oral administration, the daily dosage is as a rule about 0.01 to 20 mg/kg, preferably 0.1 to 10 mg/kg of body weight. If appropriate, it may be necessary to deviate from the amounts mentioned. If relatively large amounts are administered, it is advisable to divide the daily dose into several part administrations, for example two or three, distributed over the course of the day.

In addition to the compounds of the general formula I, the pharmaceutical products can also contain one or more other pharmaceutically active substances, for example agents which promote circulation, such as dihydroergocristine, nicergoline, buphenine, nicotinic acid and its esters, pyridylcarbinol, bencyclane, cinnarizine, naftidrofuryl, raubasine and vincamine; positively inotropic compounds, such as digoxin, acetalydigoxin, metildigoxin and lanto-glycosides; coronary dilators, such as carbocromen, dipyridamole, nifedipine and perhexiline; antianginal compounds, such as isosorbide dinitrate, isosorbide mononitrate, glycerol trinitrate, molsidomine and verapamil; β-blockers, such as propranolol, oxprenolol, atenolol, metoprolol and penbutolol, and oogenically metabolic agents, such as pirilinol.

The following Examples 1 to 19 relate to the preparation of compounds of the formula II and VI, Examples 20 to 79 relate to the preparation of compounds of the formula I, and Examples A to H relate to the preparation of formulations of the compounds of the formula I.

EXAMPLE 1

4-((2-Oxo-pyrrolidin-1-yl)-phenyl)-4-oxo-3-methyl-2-butenoic acid 66.7 g (0.5 mole) of anhydrous aluminum chloride are suspended in 150 ml of carbon disulphide. 32.2 g (0.2 mole) of N-phenyl-pyrrolidin-2-one and 22.4 g (0.2 mole) of methylmaleic anhydride are added, while stirring and cooling. The mixture is heated under reflux until a viscous mass is formed, and this is left to stand at room temperature for 40 hours, the solvent is decanted off and the mixture is decomposed carefully with icewater and concentrated aqueous hydrochloric acid and extracted with methylene cchloride or ethyl acetate. The organic phase is extracted with dilute sodium hydroxide solution, the aqueous phase is clarified by filtration, acidified with acetic acid and extracted and the extract is concentrated. The resulting oil is further reacted directly.

Yield: 37.6 g (69% of theory).

EXAMPLE 2

4-((2-Oxo-pyrrolidin-1-yl)-phenyl)-4-oxo-3-methyl-butyric acid 27.3 g (0.1 mole) of the compound obtained in Example 1 are dissolved in 200 ml of water and 15 ml of acetic acid. After addition of 15 g (0.23 mole) of zinc dust, the mixture is heated under reflux for 30 minutes and filtered. The aqueous phase is rendered alkaline and extracted, the extract is acidified and the resulting oil is separated off.

Yield: 12.7 g (46% of theory).

EXAMPLE 3

Methyl (4-(4-(2-imidazol-1-yl)-ethoxy)-phenyl)-4-oxo-3-methyl-butyrate 40 g (0.3 mole) of anhydrous aluminium chloride are suspended in 100 ml of anhydrous 1,2-dichloroethane and the suspension is cooled to 10° C. 16.5 g (0.1 mole) of 4-methoxy-carbonyl-2-methyl-butyryl chloride in 50 ml of 1,2-dichloroethane and 18.8 g (0.1 mole) of 1-(2-phenoxy)-ethyl-imidazole in 50 ml of 1,2-dichloroethane are added, with cooling. The mixture is stirred at room temperature for 16 hous, hydrolysed with icewater and aqueous concentrated hydrochloric acid. After addition of 27% strenght sodium hydroxide solution, the mixture is rapidly extracted at pH 13 and the extract is dried and concentrated.

Yield: 28.3 g (90% of theory).

EXAMPLE 4

4-(4-(2-Oxo-imidazolidin-1-yl)-phenyl)-4-oxo-3-methyl-butyric acid 20 g (0.15 mole) of anhydrous aluminium chloride are dissolved in 100 ml of nitrobenzene. 8.1 g (0.05 mole) of 2-oxo-1-phenyl-imidazolidine and 8.2 g (0.05 mole) of 3-methoxycarbonyl-2-methyl-butyryl chloride in 100 ml of nitrobenzene are added dropwise at 5° C. in the course of 1 hour. After a reaction time of 20 hours at 50° C., the mixture is hydrolysed and extracted with ethyl acetate and the extract is dried and concentrated.

380 ml of 0.7% strength aqueous sodium hydroxide solution are added to the resulting ester and the mixture is stirred at room temperature for 20 hours. After extraction with methylene chloride, the mixture is clarified by filtration, the filtrate is acidified to pH 1 with hydrochloric acid and the product is separated off and recrystallised.

Yield: 4.1 g (30% of theory), melting point: 166°–167° C.

All the ketocarboxylic acid derivatives of the formula II required can be prepared analogously to the above examples. Examples which may be mentioned are:

5. 4-(4-(3-Oxo-pyrazolidin-1-yl)-phenyl)-4-oxo-3-methyl-butyric acid and its methyl ester
6. 4-(3-Methyl-1-phenyl-5-oxo-pyrazol-4-yl)-4-oxo-3-methyl-butyric acid and its methyl ester
7. 4-(4-((2-Oxo-oxazolidin-5-yl)-methoxy)-phenyl)-4-oxo-3-methyl-butyric acid and its methyl ester
8. 4-(3-(2,4-Dioxo-imidazolidin-1-yl)-4-methoxy-phenyl)-4-oxo-3-methyl-butyric acid and its methyl ester
9. 4-(4-(2-(2-Oxo-pyrrolidin-1-yl)-ethyl)-amino-carbonyl-aminophenyl)-4-oxo-3-methyl-butyric acid and its methyl ester
10. 4-(2-Methoxyethoxy-phenyl)-4-oxo-3-methyl-butyric acid and its methyl, ethyl and n-propyl esters.
11. 4-(4-Amino-1,3-dimethyl-pyrazol-4-yl)-4-oxo-3-methyl-butyric acid and its methyl ester
12. 4-(4-(3-Pyridyl-methoxy)-phenyl)-4-oxo-3-methyl-butyric acid and its methyl ester
13. 4-(4-(Aminocarbonyl-methoxy)-phenyl)-4-oxo-3-methyl-butyric acid and its methyl ester
14. 4-(4-Methylthio-phenyl)-4-oxo-3-methyl-butyric acid and its methyl, ethyl and n-propyl esters
15. 4-(4-(5-Methyl-1,3,4-oxadiazol-2-yl)-methoxy-phenyl)-4-oxo-3-methyl-butyric acid and its methyl ester
16. 4-(4-(2-Hydroxy-4-methyl-pyrid-6-yl)-methoxy-phenyl)-4-oxo-3-methyl-butyric acid and its methyl ester
17. 4-(4-(2-(2-Methoxy-carbonyl-pyrrolidin-1-yl)-ethoxy)-phenyl)-4-oxo-3-methyl-butyric acid and its methyl ester
18. 4-(4-(2,5-Dioxo-pyrrolidin-1-yl)-phenyl)-4-oxo-3-methyl-butyric acid and its methyl ester
19. 4-(3-Indolyl)-4-oxo-3-methyl-butyric acid and its methyl, ethyl and n-propyl esters

EXAMPLE 20

6-(4-(2-(Imidazol-1-yl)-ethoxy)-phenyl)-5-methyl-4,5-dihydro-3(2H)-pyridazinone 12.7 g (0.04 mole) of the compound prepared in Example 3 and 3 ml (0.06 mole) of hydrazine hydrate are heated in 100 ml of methanol at room temperature for 30 minutes and then under reflux for 2 hours. After the mixture has been concentrated, aqueous sodium carbonate solution and methylene chloride are added, the organic phase is separated off and concentrated and the residue is recrystallized from isopropanol.

Yield: 2.9 g (24% of theory), melting point: 151°–153° C.

Elemental analysis: $C_{16}H_{18}N_4O_2$ (298.35), calculated: C 64.4, H 6.1, N 18.8, O 10.7, found: C 63.9, H 5.9, N 18.9, O 11.0.

EXAMPLE 21

6-(4-(2-Oxo-pyrrolidin-1-yl)-phenyl)-5-methyl-4,5-dihydro-3(2H)-pyridazinone 6.9 g (0.025 mole) of the compound prepared in Example 2 are heated under reflux with 1.5 ml (0.03 mole) of hydrazine hydrate in 30 ml of ethanol for 1 hour. The product which has precipitated is filtered off with suction and recrystallised from isopropanol.

Yield: 5.5 g (81% of theory), melting point: 204°–205° C.

Elemental analysis: $C_{15}H_{17}N_3O_2$ (271.32), calculated: C 66.4, H 6.3, N 15.5, O 11.8, found: C 66.2, H 5.9, N 15.4, O 12.1.

EXAMPLE 22

6-(4-(2-Oxo-imidazolidin-1-yl)-phenyl)-5-methyl-4,5-dihydro-3(2H)-pyridazinone 4 g (0.014 mole) of the compound prepared in Example 4 are stirred with 1 ml (0.021 mole) of hydrazine hydrate in 30 ml of ethanol and 20 ml of dimethylformamide at 80° C. for 2 hours. After the mixture has been cooled, the product is filtered off with suction and recrystallised from dimethylformamide.

Yield: 0.6 g (16% of theory), melting point: 322°–325° C.

Elemental analysis: $C_{14}H_{16}N_4O_2$ (272.31), calculated: C 61.8, H 5.9, N 20.6, O 11.8, found: C 61.4, H 6.1, N 20.7, O 11.7.

EXAMPLE 23

6-(4-(2-Methoxy-ethoxy)-phenyl)-4,5-dihydro-3(2H)-pyridazinone 6 g (0.024 mole) of 4-(4-(2-methoxy-ethoxy)-phenyl)-4-oxo-butyric acid and 1.2 g (0.024 mole) of hydrazine hydrate are stirred in 90 ml of ethanol at 50° C. for 1 hour. After the mixture has been cooled, the product is filtered off with suction, washed with ethanol and dried.

Yield: 5.2 g (88% of theory), melting point: 146°–148° C.

Elemental analysis $C_{13}H_{16}N_2O_3$ (248.28), calculated: C 62.9, H 6.5, N 11.3, O 19.3, found: C 63.4, H 6.4, N 11.3, O 19.0.

EXAMPLE 24

6-(4-(2-Oxo-pyrrolidin-1-yl)-phenyl)-4,5-dihydro-3(2H)-pyridazinone 10.4 g (0.04 mole) of 4-(4-(2-oxo-pyrrolidin-1-yl)-phenyl)-4-oxo-butyric acid and 2 g (0.04 mole) of hydrazine hydrate are stirred under reflux in 100 ml of ethanol for 1 hour, the mixture is cooled and the product is filtered off with suction. The solid which has precipitated is stirred with sodium bicarbonate solution, filtered off with suction, washed and dried.

Yield: 9 g (87% of theory), melting point: 272°–274° C.

Elemental analysis: $C_{14}H_{15}N_3O_2$, calculated: C 65.4, H 5.9, N 16.3, O 12.4, found: C 64.7, H 6.2, N 16.2, O 12.7.

EXAMPLE 25

6-(4-(2-Oxo-imidazolin-1-yl)-phenyl)-4,5-dihydro-3(2H)-pyridazinone 7.9 g (0.03 mole) of 4-(4-(2-oxo-iminidazolidin-1-yl)-phenyl)-4-oxo-butyric acid and 1.5 g (0.03 mole) of hydrazine hydrate are heated in 100 ml of ethanol at 50° C. for 2 hours and under reflux for 3 hours. After the mixture has been cooled, the product is filtered off with suction, washed, dried and recrystallised from dimethylformamide.

Yield: 1.8 g (23% of theory), melting point: >300° C.

Elemental analysis: $C_{13}H_{14}N_4O_2$ (258.28), calculated: 60.5, H 5.5, N 21.7, O 12.4, found: C 60.3, H 5.1, N 21.7, O 12..

EXAMPLE 26

6-(4-(2-(2-Oxo-pyrrolidin-1-yl)ethyl)-amino-carbonyl-amino-phenyl)-5-methyl-4,5-dihydro-3(2H)-pyridazinone 7.2 g (0.02 mole) of 4-(4-(2-(2-oxo-pyrrolidin-1-yl)ethyl)-amino-carbonyl-amino-phenyl)-4-oxo-3-methyl-butyric acid and 1 ml (0.02 mole) of hydrazine hydrate are heated under reflux in 80 ml of ethanol and 10 ml of dimethylformamide for 2 hours. The crude product (6.3 g) which precipitates out on cooling is filtered off with suction and recrystallised from 90% strength ethanol.

Yield: 3.8 g (53% of theory), melting point: 280°–282° C.

Elemental analysis: $C_{18}H_{23}N_5O_3$ (357.42), calculated: C 60.5, H 6.5, N 19.6, O 13.4, found: C 60.5, H 6.5, N 19.8, O 13.5.

EXAMPLE 27

6-(4-Methoxy-3-(2,4-dioxo-imidazolidin-1-yl-phenyl)-5-methyl-4,5-dihydro-3(2H)-pyridazinone 8.6 g (0.027 mole) of 4-(3-(2,4-dioxo-imidazolidin-1-yl)-4-methoxy-phenyl)-4-oxo-3-methyl-butyric acid and 1.5 ml (0.031 mole) of hydrazine hydrate are heated under reflux in 100 ml of ethanol and 20 ml of dimethylformamide for 4 hours. The mixture is stirred at room temperature for a further 20 hours and the product is filtered off and recrystallised from ethanol.

Yield: 6.4 g (75% of theory), melting point: 292°–294° C.

Elemental analysis: $C_{15}H_{16}N_4O_4$ (316.32), calculated: C 57.0, H 5.1, N 17.7, O 20.2, found: C 56.1, H 5.1, N 17.2, O 21.0.

EXAMPLE 28

6-(4-(2-Oxo-oxazolidin-5-yl)-methoxy-phenyl)-5-methyl-4,5-dihydro-3(2H)-pyridazinone 5.9 g (0.019 mole) of 4-(4-(2-oxo-oxazolidin-5-yl)-methoxyphenyl)-4-oxo-3-methyl-butyric acid and 1.5 ml (0.031 mole) of hydrazine hydrate are heated under reflux in 30 ml of methanol for 1 hour.

After addition of petroleum ether, the product crystallised out. The crude product is recrystallised from 96% strength isopropanol.

Yield: 1.35 g (23% of theory), melting point: 199°–201° C.

Elemental analysis: $C_{15}H_{17}N_3O_4$ (303.32), calculated: C 59.4, H 5.6, N 13.9, O 21.1, found: C 59.8, H 5.3, N 13.4, O 21.6.

EXAMPLE 29

6-(4-(5-Hydroxy-3-methyl-1-phenyl-pyrazolyl)-5-methyl-4,5-dihydro-3(2H)-pyridazinone 4.5 g (0.016 mole) of 4-(4-(5-hydroxy-3-methyl-1-phenylpyrazolyl)-4-oxo-3-methyl-butyric acid and 1.5 ml (0.031 mole) of hydrazine hydrate are heated under reflux in 30 ml of ethanol for 1 hour. After the mixture has been concentrated, the residue is boiled up with isopropanol, the mixture is filtered and the product which has crystallised out is separated off.

Yield: 2.5 g (56% of theory), melting point: 215°–217° C.

Elemental analysis: $C_{15}H_{16}N_4O_2$ (284.32), calculated: C 63.4, H 5.7, N 19.7, O 11.3, found: C 62.3, H 5.7, N 18.6, O 11.9.

EXAMPLE 30

6-(4-(5-Methyl-1,3,4-oxadiazol-2-yl)-methoxy-phenyl)-5-methyl-4,5-dihydro-3(2H)-pyridazinone 10.1 g (0.033 mole) of 4-(4-(5-methyl-1,3,4-oxadiazol-2-yl)-methoxy-phenyl)-4-oxo-3-methyl-butyric acid and 2.1 ml (0.043 mole) of hydrazine hydrate are stirred in 100 ml of ethanol at 50° C. for 1 hour. After addition of a mixture of diethyl ether/ligroin until cloudiness results, the product crystallises out. After filtering off with suction, the product is recrystallised from 500 ml of isopropanol.

Yield: 3.3 g (33% of theory), melting point: 142°–144° C.

Elemental analysis: $C_{15}H_{16}N_4O_3$ (300.32), calculated: C 60.0, H 5.4, N 18.7, O 16.0, found: C 60.6, H 5.8, N 18.8, O 15.2.

EXAMPLE 31

6-(4-(2-Hydroxyethyl)-amino-phenyl)-5-methyl-4,5-dihydro-3(2H)-pyridazinone 2.2 g (0.009 mole) of 4-(4-(2-hydroxyethyl)-amino)-phenyl-4-oxo-3-methyl-butyric acid and 1.0 ml (0.02 mole) of hydrazine hydrate are stirred in 10 ml of methanol at 50° C. for 3 hours. After cooling, the product is filtered off with suction and dried.

Yield: 1.1 g (51% of theory), melting point: 176°–178° C.

Elemental analysis: $C_{13}H_{17}N_3O_2$ (247.30), calculated: C 63.1, H 6.9, N 17.0, O 12.9, found: C 63.3, H 7.0, N 16.9, O 13.1.

EXAMPLE 32

6-(3-Indolyl)-5-methyl-4,5-dihydro-3(2H)-pyridazinone 7.0 g (0.03 mole) of 4-(3-(indolyl)-4-oxo-3-methyl-butyric acid and 1.7 ml (0.035 mole) of hydrazine hydrate are heated under reflux in 60 ml of ethanol for 2 hours. After the mixture has been concentrated, the residue is chromatographed over a silica gel column with methylene chloride:methanol=9:1 as the eluant and the product is recrystallised from isopropanol.

Yield: 1.5 g (22% of theory), melting point: 257°–259° C.

Elemental analysis: $C_{13}H_{13}N_3O$ (227.27), calculated: C 68.7, H 5.8, N 18.5, O 7.0, found: C 68.3, H 5.7, N 18.1, O 7.3.

EXAMPLE 33

6-(4-Hydroxycarbonyl-methoxy)-phenyl-5-methyl-4,5-dihydro-3(2H)-pyridazinone 8.0 g (0.03 mole) of (4-(4-hydroxycarbonyl-methoxy)-phenyl)-4-oxo-3-methylbutyric acid and 2.5 ml (0.052 mole) of hydrazine hydrate are heated under reflux in 100 ml of n-propanol for 1 hour.

After the mixture has been concentrated, sodium bicarbonate solution is added, the mixture is extracted with methylene chloride, the aqueous phase is acidified and the product which has precipitated is recrystallised from isopropanol.

Yield: 1.7 g (22% of theory), melting point: 224°–226° C.

Elemental analysis: $C_{13}H_{14}N_2O_4$ (262.27), calculated: C 59.5, H 5.4, N 10.7, O 24.4, found: C 59.1, H 5.2, N 10.8, O 24.6.

EXAMPLE 34

6-(4-Methylthio-phenyl)-5-methyl-4,5-dihydro-3(2H)-pyridazinone 2.3 g (0.01 mole) of 4-(4-methylthio-phenyl)-4-oxo-3-methyl-butyric acid and 1 ml of hydrazine hydrate are heated under reflux in 20 ml of isopropanol for 2 hour. After the mixture has been cooled, the product is filtered off with suction and dried.

Yield: 1.8 g (80% of theory), melting point: 199°-201° C.

Elemental analysis: $C_{12}H_{14}N_2OS$ (234.32), calculated: C 61.5, H 6.0, N 12.0, O 6.8, found: C 61.8, H 6.0, N 12.1, O 6.7.

EXAMPLE 35

6-(4-(3-Pyridylmethyl)-phenyl)-5-methyl-4,5-dihydro-3(2H)-pyridazinone hydrochloride 7.1 g (0.025 mole) of 4-(4-(3-pyridylmethyl)-phenyl)-4-oxo-3-methyl-butyric acid and 1.5 ml (0.03 mole) of hydrazine hydrate are stirred in 30 ml of ethylene glycol monomethyl ether at 100° C. for 1 hour. After addition of ethanolic hydrochloric acid, the product is filtered off with suction and recrystallised from 96% strength ethanol.

Yield: 4.4 g (56% of theory), melting point: 225°-226° C.

Elemental analysis: $C_{17}H_{18}ClN_3O$ (315.81), calculated: C 64.7, H 5.7, Cl 11.2, N 13.3, O 5.1, found: C 65.1, H 5.7, Cl 11.8, N 13.5, O 5.2.

The following 4,5-dihydro-3(2H)-pyridazinones of the formula I, for example, can be prepared analogously to the above examples:

EXAMPLE 36

6-(4-(2,5-Dioxo-pyrrolidin-1-yl)-5-methyl-4,5-dihydro-3(2H)- pyridazinone

Solvent: ethanol
Reaction temperature: 75° C.
Yield: 62% of theory,
Melting point: 225° to 227° C.

EXAMPLE 37

6-(4-(5-Amino-1,3-dimethyl-pyrazolyl)-5-methyl-4,5-dihydro-3(2H)-pyridazinone

Solvent: n-butanol.
Reaction temperature: 100° C.
Yield: 66% of theory.

EXAMPLE 38

6-(4-(3-Pyridyl)-methoxy-phenyl)-5-methyl-4,5-dihydro-3(2H)-pyridazinone

Solvent: n-pentanol.
Reaction temperature: 70° C.
Yield: 43% of theory.
Melting point: hydrochloride 217° to 218° C.

EXAMPLE 39

6-(4-Aminocarbonyl)-methoxy-phenyl)-5-methyl-4,5-dihydro-3(2H)-pyridazinone

Solvent: dimethylformamide.
Reaction temperature: 100° C.
Yield: 63% of theory.
Melting point: 226° to 227° C.

EXAMPLE 40

6-(4-((2-Methoxy-ethyl)-amino-carbonyl)-methoxy-phenyl)-5-methyl-4,5-dihydro-3(2H)-pyridazinone Solvent: dimethyl sulphoxide.
Reaction temperature: 90° C.
Yield: 51% of theory.
Melting point: 182° to 183° C.

EXAMPLE 41

6-(4-(2,4-Dioxo-imidazolidin-1-yl)-phenyl)-5-methyl-4,5-dihydro-3(2H)-pyridazinone Solvent: ethylene glycol.
Reaction temperature: 160° C.
Yield: 34% of theory.

EXAMPLE 42

6-(4-(4-Methyl-2-hydroxy-pyridyl-6-yl)-methoxy-phenyl)-5-methyl-4,5-dihydro-3(2H)-pyridazinone Solvent: 1,4-dioxane.
Reaction temperature: 70° C.
Yield: 47% of theory.
Melting point: 127° to 128° C.

EXAMPLE 43

6-(4-(2-(2-Methoxycarbonyl-pyrrolidin-1-yl)-ethoxy)-phenyl)-5-methyl-4,5-dihydro-3(2H)-pyridazinone Solvent: dibutyl ether.
Reaction temperature: 140° C.
Yield: 82% of theory.

EXAMPLE 44

6-(4-(2-Oxo-imidazolidin-1-yl)-phenyl)-2,5-dimethyl-3(2H)-pyridazinone

Solvent: pyridine.
Reaction temperature: 60° C.
Yield: 78% of theory.

EXAMPLE 45

6-(4-(3-Oxo-pyrazolidin-1-yl)-phenyl)-5-methyl-4,5-dihydro-3(2H)-pyridazinone

Solvent: cyclohexanol.
Reaction temperature: 65° C.
Yield: 25% of theory.
Melting point: 154° to 155° c.

EXAMPLE 46

6-(4-Methyl-sulphonyl-phenyl)-5-methyl-4,5-dihydro-3(2H)-pyridazinone

Solvent: 1,2-dimethoxyethane.
Reaction temperature: 50° C.
yield: 54% of theory.

EXAMPLE 47

6-(4-Methyl-sulphinyl-phenyl)-5-methyl-4,5-dihydro-3(2H)-pyridazinone

Solvent: xylene
Reaction temperature: 90° C.
Yield: 87% of theory

EXAMPLE 48

6-(2-(Pyrrolyl)-5-methyl-4,5-dihydro-3(2H)-pyridazinone

Solvent: tetrahydrofuran

Reaction temperature: 60° C.
Yield: 38% of theory
Melting point: 196° to 198° C.

EXAMPLE 49

6-(3-Indolyl)-2-isopropyl-5-methyl-4,5-dihydro-3(2H)-pyridazinone

Solvent: acetonitrile
Reaction temperature: 80° C.
Yield: 73% of theory

EXAMPLE 50

6-(4-(4-Methyl-2-oxo-pyran-6-yl)-methoxy-phenyl)-5-methyl-4,5-dihydro-3(2H)-pyridazinone Solvent: chlorobenzene
Reaction temperature: 70° C.
Yield: 47% of theory

EXAMPLE 51

6-(4-(2-Oxo-oxazolidin-3-yl)-phenyl)-5-methyl-4,5-dihydro-3(2H)-pyridazinone

Solvent: chloroform
Reaction temperature: 60° C.
Yield: 31% of theory

EXAMPLE 52

6-(1,4-Dihydro-2-oxo-benz(d)(1,3)-oxazin-6-yl)-5-methyl-4,5-dihydro-3(2H)-pyridazinone Solvent: N-methylpyrrolidone
Reaction temperature: 40° C.
Yield: 25% of theory

EXAMPLE 53

6-(L-4-Thiazolidin-4-yl-carbonyl-amino-phenyl)-5-methyl-4,5-dihydro-3(2H)-pyridazinone 1.9 g (0.014 mole) of L-thiazolidine-4-carboxylic acid, 2.9 g (0.014 mole) of 6-(4-amino-phenyl)-5-methyl-4,5-dihydro-3(2H)-pyridazinone and 8 ml of triethylamine are dissolved in 10 ml of dimethylformamide. After cooling to 0° to 5° C., 5 ml (0.03 mole) of methylethyl-phosphinic anhydride are slowly added dropwise. The mixture is stirred at room temperature and hydrolysed with aqueous sodium bicarbonate solution and the product which has precipitated is recrystallised from isopropanol.

Yield: 1.1 g (25% of theory), melting point: 214°–216° C.

Elemental analysis: $C_{15}H_{18}N_4O_2S$ (318.40),

| | C | H | N | O |
|---|---|---|---|---|
| calculated: | 56.6 | 5.7 | 13.6 | 10.0 |
| found: | 55.9 | 5.5 | 13.6 | 10.2 |

EXAMPLE 54

6-(4-(3-tert.-Butoxycarbonyl-L-thiazolidin-4-yl-carbonyl-amino)phenyl)-5-methyl-4,5-dihydro-3(2H)-pyridazinone 9.3 g (0.04 mole) of 3-tert.-butoxycarbonyl-L-thiazolidine-4-carboxylic acid and 7.0 g (0.04 mole) of 1,1'-carbonyl-di-1,2,4-triazole are stirred in 15 ml of N-methylpyrrolidinone at 60° C. for 15 minutes. After addition of 7.1 g (0.035 mole) of 6-(4-aminophenyl)-5-methyl-4,5-dihydro-3(2H)-pyridazinone the mixture is stirred at room temperature for 6 hours, water is added, the mixture is extracted, the extract is crystallised with methanol and the product is recrystallised from methanol/ethyl acetate. Yield: 6.5 g (39% of theory), melting point: 200° to 201° C.

Elemental analysis: $C_{20}H_{26}N_4O_4S$ (418.52),

| | C | H | N | O | S |
|---|---|---|---|---|---|
| calculated: | 57.4 | 6.3 | 13.4 | 15.3 | 7.7 |
| found: | 57.3 | 6.0 | 13.1 | 15.6 | 7.6 |

EXAMPLE 55

6-(4-(3-Benzyloxycarbonyl-L-thiazolidin-4-yl-carbonyl-amino)-phenyl)-5-methyl-4,5-dihydro-3(2H)-pyridazinone 8.0 g (0.03 mole) of 3-benzyloxycarbonyl-L-thiazolidine-4-carboxylic acid and 4.9 g (0.03 mole) of N,N'-carbonyl-diimidazole are stirred in 10 ml of dimethylformamide at 60° C. for 10 minutes. After addition of 5.1 g (0.025 mole) of 6-(4-aminophenyl)-5-methyl-4,5-dihydro-3(2H)-pyridazinone, the mixture is stirred at room temperature for 18 hours and concentrated, aqueous sodium bicarbonate solution is added, the mixture is extracted with methylene chloride and the extract is chromatographed over a silica gel column (eluant: methylene chloride:methanol = 95:5).

Yield: 7.7 g (43% of theory).

Elemental analysis $C_{23}H_{24}N_4O_4S$ (452.54),

| | C | H | N | O |
|---|---|---|---|---|
| calculated: | 61.0 | 5.3 | 12.4 | 14.1 |
| found: | 60.5 | 5.3 | 12.5 | 14.1 |

The N,N'-carbonyl-diimidazole can be replaced, with similarly good success, by an equivalent amount of 2,2'-carbonyl-di-1,2,3-triazole, 1,1'-carbonyl-di-1,2,4-triazole, 1,1'-carbonyl-di-pyrazole, 2,2'-carbonyl-di-tetrazole, N,N'-carbonyl-di-benzimidazole or N,N'-carbonyl-di-benzotriazole.

EXAMPLE 56

6-(4-(5-Oxo-perhydro-(1,4)-thiazepin-3-yl-carbonyl-amino)-phenyl)-5-methyl-4,5-dihydro-3(2H)-pyridazinone 5.3 g (0.03 mole) of 5-oxo-perhydro-(1,4)-thiazepine-3-carboxylic acid and 6.1 g (0.03 mole) of N,N'-carbonyl-diimidazole are stirred in 15 ml of dimethylformamide at 50° c. for 15 minutes. After addition of 4.9 g (0.03 mole) of 6-(4-amino-phenyl)-5-methyl-4,5-dihydro-3(2H)-pyridazinone, the mixture is stirred at room temperature for 12 hours and the product is filtered off with suction and dried.

Yield: 6.0 g (55% of theory), melting point: 272° to 274° C.

Elemental analysis $C_{17}H_{20}N_4O_3S$ (360.44),

| | C | H | N | O | S |
|---|---|---|---|---|---|
| calculated: | 56.7 | 5.6 | 15.5 | 13.3 | 8.9 |
| found: | 56.7 | 5.4 | 15.6 | 13.6 | 8.8 |

EXAMPLE 57

6-(4-(3-tert.-Butoxycarbonyl-thiazolidin-2-yl-carbonyl-amino)-phenyl)-5-methyl-4,5-dihydro-3(2H)-pyridazinone 7.5 g (0.032 mole) of 3-tert.-butoxycarbonyl-thiazolidine-2-carboxylic acid and 5.2 g (0.032 mole) of N,N'-carbonyl-diimidazole are heated under reflux in 50 ml of tetrahydrofuran for 15 minutes. After addition of 6.1 g (0.03 mole) of 6-(4-aminophenyl)-5-methyl-4,5-dihydro-3(2H)-pyridazinone, the mixture is stirred at room temperature for 18 hours and concentrated and the residue is crystallised with ethyl acetate.

yield: 4.8 g (38% of theory), melting point: 225° to 226° C.

Elemental analysis $C_{20}H_{26}N_4O_4S$ (418.52),

|  | C | H | N | O | S |
|---|---|---|---|---|---|
| calculated: | 57.4 | 6.3 | 13.4 | 15.3 | 7.7 |
| found: | 57.4 | 5.6 | 13.7 | 15.2 | 7.7 |

EXAMPLE 58

6-(4-(4-Chlorophenoxyacetylamino)-phenyl)-5-methyl-4,5-dihydro-3(2H)-pyridazinone 0.1 g of 4-dimethylaminopyridine and 5.1 g (0.025 mole) of 4-chlorophenoxyacetyl chloride are added to 5.1 g (0.025 mole) of 6-(4-amino-phenyl)-5-methyl-4,5-dihydro-3(2H)-pyridazinone in 20 ml of pyridine. The mixture is stirred at room temperature for 5 hours and concentrated, water is added and the mixture is extracted with methylene chloride.

Yield: 6.0 g (65% of theory), melting point: 226° to 227° C.

Elemental analysis $C_{19}H_{18}ClN_3O_3$ (371.82),

|  | C | H | Cl | N | O |
|---|---|---|---|---|---|
| calculated: | 61.4 | 4.9 | 9.5 | 11.3 | 12.9 |
| found: | 60.7 | 4.8 | 9.0 | 11.4 | 13.2 |

EXAMPLE 59

6-(4-(Thiazolidin-2-yl-carbonyl-amino-phenyl)-5-methyl-4,5-dihydro-3(2H)-pyridazinone hydrochloride 15 ml of ice-cold trifluoroacetic acid are added to 4.2 g (0.01 mole) of 6-(4-(3-tert.-butoxycarbonyl-thiazolidin-2-yl-carbonylamino)-phenyl)-5-methyl-4,5-dihydro-3(2H)-pyridazinone at 0° C. The mixture is neutralised in an ice-bath with sodium hydroxide solution, brought to pH 4 with potassium bisulphate solution and extracted with methylene chloride. After addition of methanolic hydrochloric acid, the product which has precipitated is filtered off with suction and recrystallised from isopropanol/ethyl acetate.

Yield: 1.9 g (54% of theory), melting point: 233° to 234° C.

Elemental analysis $C_{15}H_{19}ClN_4O_2S$ (354.86),

|  | C | H | N | O |
|---|---|---|---|---|
| calculated: | 50.8 | 5.4 | 15.8 | 9.0 |
| found: | 50.5 | 5.6 | 15.4 | 9.1 |

EXAMPLE 60

6-(4-(2,4-Dioxo-imidazolidin-3-yl)-acetylamino-phenyl)-5-methyl-4,5-dihydro-3(2H)-pyridazinone 4.8 g (0.03 mole) of hydantoyl-3-acetic acid and 4.9 g (0.03 mole) of carbonyldiimidazole are stirred in 20 ml of toluene at 80° C. for 15 minutes. After addition of 6.1 g (0.03 mole) of 6-(4-amino-phenyl)-5-methyl-4,5-dihydro-3(2H)-pyridazinone, stirring is continued at room temperature for 24 hours and the product is precipitated with isopropanol, filtered off with suction and chromatographed over a silica gel column (eluant methylene chloride:methanol=9:1).

Yield: 1.5 g (15% of theory),

Elemental analysis $C_{16}H_{17}N_5O_4$ (343.34),

|  | C | H | N | O |
|---|---|---|---|---|
| calculated: | 56.0 | 5.0 | 20.4 | 18.6 |
| found: | 55.6 | 5.1 | 20.2 | 19.0 |

EXAMPLE 61

6-(4-(S-(4-Pyridyl)-thioacetylamino)-phenyl)-5-methyl-4,5-dihydro-3(2H)-pyridazinone hydrochloride 3.4 g (0.03 mole) of S-4-pyridylmercapto-acetic acid and 3.3 g (0.02 mole) of N,N'-carbonyldiimidazole are stirred in 20 ml of dimethylformamide (DMF) at 60° C. for 15 minutes. After addition of 4.1 g (0.02 mole) of 6-(4-amino-phenyl)-5-methyl-4,5-dihydro-3(2H)-pyridazinone, the mixture is stirred at room temperature for 5 hours, water is added and the product is filtered off with suction.

The product is dissolved in 96% strength ethanol, the solution is filtered, ethanolic hydrochloric acid is added and the product is filtered off with suction.

Yield: 5.8 g (74% of theory), melting point: 278° to 280° C.

Elemental analysis $C_{18}H_{19}ClN_4O_2S$ (390.89),

|  | C | H | Cl | N | O | S |
|---|---|---|---|---|---|---|
| calculated: | 55.3 | 4.9 | 9.1 | 14.3 | 8.2 | 8.2 |
| found: | 55.3 | 4.9 | 9.2 | 14.0 | 8.1 | 8.3 |

EXAMPLE 62

6-(4-(2,4-Dioxo-imidazolidin-5-yl)-acetylamino-phenyl)-5-methyl-4,5-dihydro-3(2H)-pyridazinone 3.2 g (0.02 mole) of hydantoyl-5-acetic acid and 3.3 g (0.02 mole) of N,N'-carbonyldiimidazole are stirred in 10 ml of dimethyl sulphoxide at room temperature for 10 minutes. After addition of 4.1 g (0.02 mole) of 6-(4-aminophenyl)-5-methyl-4,5-dihydro-3(2H)-pyridazinone, stirring is continued for 24 hours, water is added and the product is filtered off with suction and recrystallised from acetic acid.

Yield: 2.5 g (36% of theory), melting point: 267° to 270° C.

Elemental analysis $C_{16}H_{17}N_5O_4$ (343.34),

|  | C | H | N | O |
|---|---|---|---|---|
| calculated: | 56.0 | 5.0 | 20.4 | 18.6 |
| found: | 56.8 | 5.2 | 20.1 | 18.2 |

The compounds given in the following Examples 63 to 79 can be prepared analogously to the above Examples 54 to 62:

EXAMPLE 63

6-(4-(Perhydro-1,4-thiazin-3-yl)-carbonyl-amino)-phenyl-5-methyl-4,5-dihyro-3(2H)-pyridazinone Solvent: dioxane.
Reaction temperature: 70° C.
Yield: 53% of theory.

EXAMPLE 64

6-(4-(Perhydro-4-formyl-1,4-thiazin-3-yl)-carbonyl-amino)-phenyl-5-methyl-4,5-dihydro-3(2H)-pyridazinone Solvent: tetrahyrofuran.
Reaction temperature: 60° C., Yield: 68% of theory.

EXAMPLE 65

6-(4-Perhydro-3-oxo-1,4-thiazin-5-yl)-carbonyl-amino)-phenyl-5-methyl-4,5-dihydro-3(2H)-pyridazinone Solvent: dimethylformamide.
Reaction temperature: 100° C.
Yield: 71% of theory.

EXAMPLE 66

6-(4-(3-Formyl-thiazolidin-4-yl)-carbonyl-amino)-phenyl-5-methyl-4,5-dihydro-3(2H)-pyridazinone Solvent: ethylene glycol dimethyl ether.
Reaction temperature: 85° C.
Yield: 42% of theory.

EXAMPLE 67

6-(4-(3-Acetyl-thiazolidin-4-yl)-carbonyl-aminio)-phenyl-5-methyl-4,5-dihydro-3(2H)-pyridazinone Solvent: diethylene glycol dimethyl ether.
Reaction temperature: 100° C.
Yield: 49% of theory.

EXAMPLE 68

6-(4-(Perhydro-1,3-thiazin-4-yl)-carbonyl-amino)-phenyl-5-methyl-4,5-dihydro-3(2H)-pyridazinone Solvent: dimethyl sulphoxide.
Reaction temperature: 110° C.
Yield: 27% of theory.

EXAMPLE 69

6-(4-(Perhydro-3-tert.-butoxycarbonyl-1,3-thiazin-4-yl)-carbonylamino)-phenyl-5-methyl-4,5-dihydro-3(2H)-pyridazinone Solvent: methylene chloride.
Reaction temperature: 40° C.
Yield: 49% of theory.

EXAMPLE 70

6-(4-(Perhydro-3-formyl-1,3-thiazin-4-yl)-carbonyl-amino)-phenyl-5-methyl-4,5-dihydro-3(2H)-pyridazinone Solvent: hexamethylphosphoric acid triamide.
Reaction temperature: 90° C.
Yield: 65% of theory.

EXAMPLE 71

6-(4-(2-Oxo-thiazolidin-4-yl)-carbonyl-amino)-phenyl-5-methyl-4,5-dihydro-3(2H)-pyridazinone Solvent: methanol.
Reaction temperature: 25° C.
Yield: 25% of theory.

EXAMPLE 72

6-(4-(Thiazolidin-2-yl)-carbonyl-amino)-phenyl-5-methyl-4,5-dihydro-3(2H)-pyridazinone Solvent: chlorobenzene.
Reaction temperature: 120° C.
Yield: 32% of theory.

EXAMPLE 73

6-(4-(1-Oxido-3-oxo-perhydro-1,4-thiazin-5-yl)-carbonyl-amino)phenyl-5-methyl-4,5-dihydro-3(2H)-pyridazinone Solvent: ethanol.
Reaction temperature: 80° C.
Yield: 39% of theory.

EXAMPLE 74

6-(4-(1-Oxido-3-oxo-perhydro-1,4-thiazin-5-yl)-carbonyl-amino)phenyl-5-methyl-4,5-dihydro-3(2H)-pyridazinone Solvent: dimethylformamide.
Reaction temperature: 90° C.
Yield: 84% of theory.

EXAMPLE 75

6-(4-(1-Oxido-5-oxo-perhydro-1,4-thiazepin-3-yl)-carbonyl-amino)phenyl-5-methyl-4,5-dihydro-3(2H)-pyridazinone Solvent: acetonitrile,
Reaction temperature: 81° C.
Yield: 61% of theory.

EXAMPLE 76

6-(4-(3-Pyridyl-oxy)-acetylamino)-phenyl-5-methyl-4,5-dihydro-3(2H)-pyridazinone Solvent: pyridine,
Reaction temperature: 115° C.
Yield: 75% of theory.

EXAMPLE 77

6-(4-(3-Pyridyl-methoxy)-acetylamino)-phenyl-5-methyl-4,5-dihydro-3(2H)-pyridazinone Solvent: ethylene glycol monomethyl ether.
Reaction temperature: 100° C.
Yield: 42% of theory.

EXAMPLE 78

6-(4-(4-Pyridyl-sulphinyl)-acetylamino)-phenyl-5-methyl-4,5-dihydro-3(2H)-pyridazinone Solvent: dioxane.
Reaction temperature: 70° C.
Yield: 67% of theory.

EXAMPLE 79

6-(4-(4-Pyridyl-sulphonyl)-acetylamino)-phenyl-5-methyl-4,5-dihydro-3(2H)-pyridazinone Solvent: N-methylpyrrolidone.

Reaction temperature: 100° C.
Yield: 48% of theory.

The following examples illustrate the composition of formulations of the 4,5-dihydro-3(2H)-pyridazinones according to the invention.

|  | per tablet |
|---|---|
| Example A | |
| Tablets | per tablet |
| Active compound (finely ground) | 50 mg |
| Lactose | 150 mg |
| Maize starch, white | 230 mg |
| Polyvinylpyrrolidone | 15 mg |
| Magnesium stearate | 5 mg |
| | 450 mg |
| Example B | |
| Injection solution | |
| Active compound | 4 mg |
| Sodium chloride | 0.7 mg |
| Water for injection purposes | to 1 ml |
| Example C | |
| Rectal medicament form | |
| Active ingredient | 20 mg |
| Suppository base | to 2 g |
| Example D | |
| Emulsions | |
| Active ingredient | 60 mg |
| Glycerol, pure | 0.2–2.0 g |
| Polyethylene stearate | q.s. |
| Neutral oil | q.s. |
| Flavour correctant | q.s. |
| Demineralised water | to 100 ml |
| Example E | |
| Active compound solutions | |
| Active compound | 8 mg |
| Polyethylene glycol | 1.5 mg |
| Glycofurol | to 4 ml |
| Water for injection purposes | 6 ml |
| Example F | |
| Tablets | |
| Active compound | 20 mg |
| Lactose | 60 mg |
| Maize starch | 30 mg |
| Soluble starch | 5 mg |
| Magnesium stearate | 5 mg |
| | 120 mg |
| Example G | |
| Coated tablets | |
| Active compound | 6 mg |
| Propranolol | 40 mg |
| Lactose | 90 mg |
| Maize starch | 90 mg |
| Secondary calcium phosphate | 34 mg |
| | 260 mg |
| Example H | |
| Capsules | |
| Active compound | 5 mg |
| Prazosin | 5 mg |
| Maize starch | 185 mg |
| | 195 mg |

A low dosage of the tetrahydropyridazinone derivatives according to the invention already exhibits a particularly therapeutically useful combination of antithrombotic, cardiotonic and antianginal action with little reduction in blood pressure.

The following Tables 1 to 5 show the action data of the compounds according to the invention obtained in various in vivo and in vitro tests.

The values for the protection from arterial thromboses given in Table 1 were determined on rats by the method of Meng and Seuter (Naunyn-Schmiedeberg's Arch. Pharmacol., 301, 115 (1977)), and those for the protection from venous thromboses were determined on rabbits by the method of Harbauer ("Versuche zur Entwicklung eines standardisierten venosen Thrombosemodell am Kaninchen" ("Experiments on the development of a standardised venous thrombosis model in rabbits"), 17th Angiological Symposium in Kitzbühel, (1982)).

The values on influencing of the arachidonic acid action given in Table 2 were determined on anaesthetised guinea pigs by the method of Lefort and Vargaftig (Br. J. Pharmac. 63, 35 (1978)).

The values on inhibition of platelet aggregation given in Table 3 were determined in vitro by the method of Born (J. Physiol. 162, 67 P (1962)) using arachidonic acid, thrombin, collagen, PAF (platelet activating factor) and adenosine diphos;phate (ADP) as the aggregating agent.

The direct positive inotropic action of the substances was tested on the isolated, electrically simultaed guinea pig auricle. For this, the guinea pigs were sacrificed by a blow to the nape of the neck and the left auricle was freed and mounted in a thermostatically controlled 4-section organ bath (HSE, "Schuler" type) under an initial tension of 1 g. The contraction force of the electrically stimulated left auricle (frequency of 120/minute, voltage about 15 V, pulse width 1 msec) was recorded isometrically with Statham UC-2 force transducers and the amplified signal was recorded continuously on a 4-channel recorder (Linear Corder Mark VII, Watanable).

After stabilisation for about 60 minutes, the test substance was added in cumulative doses at intervals of 30 minutes. 4 auricles were used per substance. Each was given only one substance.

Evaluation was in each case carried ot shortly before addition of the next higher dose. X and SX were calculated from the individual values and the action of the substance, as % change, was based on the starting value before the 1st dose. The values obtained are given in Table 4.

To demonstrate the antianginal action of the compounds according to the invention, investigations were carried out on mongrel dogs of both sexes under pentobarbital anaesthesia (30 to 40 mg/kg intravenously) or under urethane/chloralose anaesthesia (3 ml/kg of urethane/chloralose mixture intravenously=20 mg/kg of chloralose and 250 mg/kg of urethane). The animals were respirated with a Bird Mark 7 respirator. The endexpiratory carbonic acid content (measured with an ultra red absorption recorder) was between 4.5 and 5% by volume. Throughout the entire experiment, the animals under pentobarbital anaesthesia were given a continuos infusion of pentobarbital intravenously=4 mg (in 6 ml)/kg/h, in order to guarantee a constant depth of anaesthesia. The animals under urethane/chloralose anaesthesia were given no continuous infusion. The infusion was made through the vena cephalica. After the experimental animals had been prepared, a period of about 1 hour was allowed to elapse, until all the haemodynamic parameters had become established (steady state). The actual experiment was then started.

The systolic and diastolic blood pressure were measured peripherally in the arteria femoralis via a Statham pressure transducer. A Millar tip catheter inserted into the left ventricle via the arteria carotis delivered the signal for the left ventricular enddiastolic pressure (=LVEDP) and the heat frequency (=HF). The rate of the increase in pressure in the left ventricle was also determined as a measure of the contractility of the heart.

The results obtained are shown in Table 5.

The comparison substance shown in the tables is amrinone.

TABLE 1

Influencing of experimental thrombosis in vivo.

| Compound of Example No. | Dose mg/kg intra-peritoneally | Protection from thrombosis (%) arterial (rats) | Protection from thrombosis (%) venous (rabbits) |
|---|---|---|---|
| 61 | 10 | 70 | 100 |
|  | 1 | 40 | 25 |
| 36 | 10 | 50 | 100 |
|  | 3 | — | 88 |
| 21 | 10 | 25 | 67 |
| 22 | 10 | — | 50 |
| 20 | 10 | 36 | 100 |
|  | 1 | — | 33 |
| 28 | 10 | — | 43 |
| 30 | 10 | 50 | 100 |
|  | 3 | — | 75 |
| 32 | 10 | — | 29 |
| 53 | 10 | 60 | 100 |
|  | 1 | 50 | 100 |
|  | 0,3 | — | 50 |
| 62 | 10 | 57 | — |
| 56 | 10 | — | 33 |
| 57 | 10 | 47 | 57 |
| 58 | 10 | 22 | 50 |
| 54 | 10 | 70 | 100 |
|  | 3 | 40 | 75 |
| Comparison substance | 10 | — | 29 |

TABLE 2

Influencing of the arachidonic acid actions (arachidonic acid, 500 ug/kg intravenously) in vivo in anaesthetised guinea pigs (change in %)

| Compound of Example No. | Dose mg/kg intra-venously | $TXA_2$-effect Broncho-spasm | $TXA_2$-effect Thrombo-cytopenia | $PGI_2$-effect Reduction in blood pressure |
|---|---|---|---|---|
| 61 | 0,01 | — | −32 | +35 |
|  | 0,03 | −19 | −90 | +32 |
| 36 | 1 | −7 | −44 | — |
|  | 3 | −11 | −43 | — |
| 21 | 0,1 | −53 | −75 | +35 |
|  | 0,3 | −67 | −73 | — |
| 20 | 1 | — | — | +70 |
| 28 | 1 | −81 | −89 | −26 |
|  | 10 | −87 | −53 | +67 |
| 30 | 1 | −36 | −75 | — |
| 53 | 0,1 | −67 | −87 | −36 |
|  | 0,3 | −82 | −100 | −26 |
| 62 | 1 | −11 | −70 | +89 |
| 56 | 1 | — | −72 | −38 |
| 57 | 0,1 | −54 | −49 | +37 |
|  | 0,3 | −74 | −71 | +49 |
| 54 | 0,01 | — | −47 | — |
|  | 0,03 | — | −69 | — |
| Comparison substance | 1 | −47 | −42 | — |

TABLE 3

Inhibition of platelet aggregation in vitro (in $IC_{50}$ umol)

| Compound of Example No. | A | B | C | D | E |
|---|---|---|---|---|---|
| 61 | 0,06 | 30 | 0,015 | 2 | 20 |
| 36 | 0,6 | 15 | — | 3 | 20 |
| 21 | 0,1 | 2 | 0,2 | 0,35 | 1 |
| 22 | 0,6 | 20 | — | — | 10 |
| 20 | 0,35 | 7 | 3,5 | 2 | 45 |
| 28 | 0,3 | 5,5 | 1 | 3 | 4 |
| 30 | 0,075 | 6 | 0.07 | 1,5 | 8 |
| 32 | 0,2 | 6,5 | — | 1,5 | 3,5 |
| 53 | 0,7 | 50 | — | 1 | 20 |
| 62 | 4,5 | — | — | — | — |
| 56 | 0,4 | 2 | — | — | 1 |
| 57 | 0,04 | 2 | 0,03 | 0,55 | 0,2 |
| 58 | 0,55 | 10 | — | — | 5 |
| 54 | 0,008 | 0,3 | 0,02 | 0,03 | 0,04 |
| Comparison substance | 9 | >100 | — | 55 | 100 |

In the above table:
A = induced by 0.36 mmol of arachidonic acid
B = induced by 10 μmol of ADP
C = induced by 0.2–0.4 N.I.H.(National Institute of Health) units/ml of thrombin
D = induced by 0.1 μmol of PAF (Platelet Activating Factor Acether)
E = induced by 5 μg/ml of collagen

TABLE 4

Determination of the cardiotonic action on the isolated left auricle of guinea pigs

| Compound of Example No. | Dose (mol) | Change in force in % |
|---|---|---|
| 21 | $10^{-3}$ | +46 |
| 22 | $10^{-4}$ | −23 |
| 20 | $10^{-3}$ | +61 |
| 28 | $10^{-3}$ | +13 |
| 30 | $10^{-3}$ | +30 |
| 32 | $10^{-3}$ | +63 |
| 53 | $10^{-3}$ | −30 |
| 56 | $10^{-3}$ | −37 |
| 57 | $3 \cdot 10^{-4}$ | +89 |
| 58 | $10^{-6}$ | +14 |
| 54 | $10^{-5}$ | +60 |
| Comparison substance | $10^{-4}$ | +34 |

TABLE 5

Cardiovascular screening on normotensive, anaesthetised dogs

| Compound of Example No. | Dose (mg/kg) | ΔBd (mmHg) systolic | ΔBd (mmHg) diastolic | ΔLVEDP (mmHg) | ΔHF (B/min) | ΔdP/dt (mmHg/s) |
|---|---|---|---|---|---|---|
| 61 | 1,0 i.v. | −75 | −45 | −2 | +14 | +300 |
| 36 | 1,0 i.d. | −30 | −20 | −9 | +35 | +2000 |
| 21 | 1,0 i.d. | −60 | −45 | −4 | +40 | +1250 |
| 22 | 5,0 i.v. | −60 | −40 | −3 | +35 | +3300 |
| 20 | 1,0 i.d. | −10 | −15 | −3 | +38 | +900 |
| 28 | 1,0 i.v. | −30 | −15 | −5 | +16 | +1500 |
| 30 | 1,0 i.v. | −50 | −25 | −3 | +19 | +2400 |
| 32 | 3,0 i.d. | −25 | −15 | −2 | +15 | +1000 |
| 53 | 5,0 i.d. | −50 | −35 | −4 | +9 | −1100 |
| 62 | 1,0 i.v. | −50 | −35 | −4 | +47 | +1100 |
| 56 | 1,0 i.v. | −40 | −40 | −9 | +33 | +2900 |

TABLE 5-continued

| Compound of Example No. | Dose (mg/kg) | ΔBd (mmHg) systolic/ diastolic | | ΔLVEDP (mmHg) | ΔHF (B/min) | ΔdP/dt (mmHg/s) |
|---|---|---|---|---|---|---|
| 57 | 1,0 i.v. | −60 | −45 | −3 | +40 | +600 |
| 58 | 1,0 i.v. | −40 | −30 | −3 | +18 | +1200 |
| Comparison | 1,0 i.v. | −10 | −15 | −1 | +15 | +750 |
| substance | 3.0 i.v. | −30 | −30 | −2 | +15 | +1250 |

In the above table:
ΔBp = change in the systolic and diastolic blood pressure
ΔLVEDP = change in the left ventricular enddiastolic pressure
ΔHF = change in heart frequency in B/minute = beats/minute
Δdp/dt = change in the rate of the increase in pressure in the left ventricle as a measure of the contractility of the heart

We claim:

1. Substituted 4,5-dihydro-3(2H)-pyridazinones of the formula I

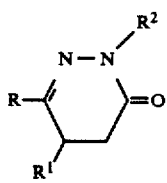

wherein R denotes a radical of the formula

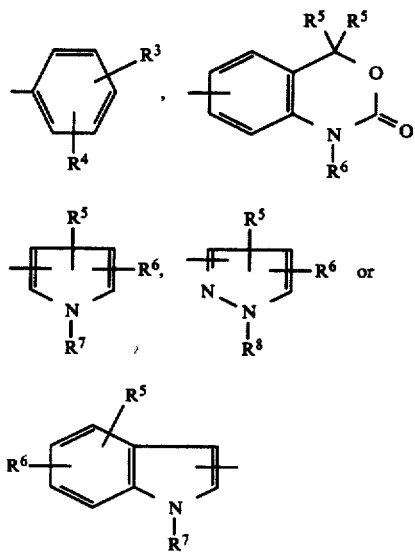

$R^1$ and $R^2$ independently of one another denote hydrogen or unsubstituted straight chain or branched chain alkyl, $R^3$ denotes alkoxy-alkoxy, amino-carbonylalkoxy, alkoxy-alkyl-amino-carbonyl-alkoxy, hydroxyalkylamino, non-urea thiazolidinyl-carbonyl-amino, monoalkylamino-carbonyl-alkoxy, alkoxy-carbonylalkoxy, hydroxy-carbonyl-alkoxy, alkyl-thio, alkyl-sulphinyl, alkyl-sulphonyl, 2-oxo-pyrrolidinyl, 2-oxopiperidinyl, 2,5-dioxo-piperidinyl, 2,5-dioxo-pyrrolidinyl, 2-oxo-imidazolidinyl, 2-oxo-hexahydro-pyrimidinyl, 2,4-dioxo-imidazolidinyl, 2,4-dioxo-hexahydropyrimidin-1-yl, 2-oxo-1,3-oxazolidinyl, 3-oxopyrazolidinyl, (2-($R^9$-carbonyl)-pyrrolidinyl-alkoxy, alkyl-substituted or alkoxy substituted by pyridyl, imidazolyl, oxadiazolyl, oxo-pyranyl, 2-hydroxy-pyridinyl, pyrrolinyl or oxo-oxazolidinyl, it being possible for the oxo-pyranyl, oxo-oxazolidinyl and oxadiazolyl in turn to be substituted by alkyl or alkoxycarbonyl, or denotes a radical of the formula $R^{10}$—CO—NH—, $R^4$ denotes hydrogen, alkyl, alkoxy, hydroxyl, alkanoyloxy or halogen, $R^5$, $R^6$ and $R^7$ independently of one another denote hydrogen, alkyl, alkoxy, hydroxy, halogen, amino, monoalkylamino or dialkylamino, $R^8$ denotes hydrogen, alkyl or phenyl, $R^9$ denotes hydroxyl, alkoxy, amino, monoalkylamino or dialkylamino, $R^{10}$ denotes p-chlorophenoxymethyl, 2,4-dioxo-imidazolidin-5-yl-methyl 2,4-dioxo-imidazolidin-3-yl-methyl, 3- pyridyl-oxymethyl, 3-pyridyl-methoxymethyl, 4-pyridyl-thiomethyl, 4-pyridyl-sulphinyl-methyl, 4- pyridyl-sulphonyl-methyl, 2-oxo-thiazolidin-4-yl, 3-oxo-perhydro-1,4-thiazin-5-yl, 1-oxido-3-oxo-perhydro-1,4-thiazin-5-yl, 5-oxo-perhydro-1,4-thiazepin-3-yl, 1-oxido-5-oxo-perhydro-1,4-thiazepin-3-yl, 1,1-dioxoido-5-oxo-perhydro-1,4-thiazepin-3-yl, or a non-urea radical of the formula

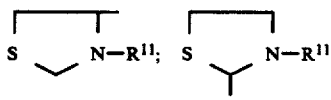

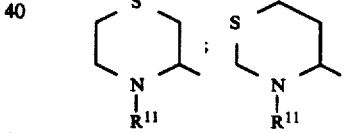

$R^{11}$ denotes hydrogen or a radical of the formula $R^{12}$—CO— and $R^{12}$ denotes hydrogen, alkyl with 1 to 5 C atoms, alkoxy with 1 to 5 C atoms, benzyl or benzyloxy, and their pharmacologically acceptable addition salts.

2. Compounds of the formula I according to claim 1, characterised in that $R^1$ and $R^2$ independently of one another denote hydrogen and/or ($C_1$–$C_4$)alkyl, $R^3$ denotes ($C_1$–$C_4$)alkoxy-($C_1$–$C_4$)alkoxy, amino-carbonyl-($C_1$–$C_4$)alkoxy, mono-($C_1$–$C_4$)alkylamino-carbonyl-($C_1$–$C_4$)alkoxy, ($C_1$–$C_4$)alkoxy-carbonyl-($C_1$–$C_4$)alkoxy, ($C_1$–$C_4$)alkoxy-($C_1$–$C_4$)alkyl-aminocarbonyl-($C_1$–$C_4$)alkoxy, hydroxy-($C_1$–$C_4$)alkylamino, non-urea thiazolidinyl-carbonyl-amino, hydroxy-carbonyl-($C_1$–$C_4$)alkoxy, ($C_1$–$C_4$)-alkoxy-carbonyl-($C_1$–$C_4$)alkoxy, hydroxy-carbonyl-($C_1$–$C_4$)alkoxy, ($C_1$–$C_4$)alkyl-thio, ($C_1$–$C_4$)alkyl-sulphinyl, ($C_1$–$C_4$)alkyl-sulphonyl, 2-oxo-pyrrolidin-1-yl, 2-oxo-piperidin-1-yl, 2,5-dioxo-piperidin-1-yl, 2,5-dioxo-pyrrolidin-1-yl, 2-oxo-imidazolin-1-yl, 2-oxo-hexa-hydro-pyrimidin-1-yl, 2,4-dioxo-imidazolin-1-yl, 2,5-dioxo-hexahydro-pyrimidin-1-yl, 2-oxo-1,3-oxazolidin-5-yl, 2-oxo-1,3-oxazolidin-1-yl, 3-oxo-pyrazlidin-1-yl, (2-($R^9$-carbonyl)-pyrrolidin-1-yl)-alkoxy, ($C_1$-$C_4$)alkyl or ($C_1$-$C_4$)alkoxy, substituted by pyridyl, imidazolyl, oxadiazolyl, oxo-pyranyl, 2-hydroxy-pyridinyl, pyrrolinyl or oxo-oxazolidinyl, it being possible for the oxo-pyranyl, oxo-oxazolidinyl and oxadiazolyl in turn to be substituted by ($C_1$-$C_4$)alkyl or ($C_1$-$C_4$)alkoxy-carbonyl, $R^4$ denotes hydrogen, ($C_1$-$C_4$)alkyl, ($C_1$-$C_4$)alkoxy, hydroxyl, alkanoyloxy with 1 to 5 C atoms, chlorine or bromine, $R^5$, $R^6$ and $R^7$ independently of one another denote hydrogen, ($C_1$-$C_4$)alkyl, ($C_1$-$C_4$)alkoxy, hydroxyl, chlorine, bromine, amino, mono-($C_1$-$C_4$)alkylamino or di($C_1$-$C_4$)alkylamino, $R^8$ denotes hydrogen, ($C_1$-$C_4$)alkyl or phenyl and $R^9$ denotes hydroxyl, ($C_1$-$C_4$)alkyl, amino, mono-($C_1$-$C_4$)alkylamino or di($C_1$-$C_4$)alkylamino.

3. Compounds of the formula I according to claim 1, characterised in that $R^1$ and $R^2$ independently of one another denote hydrogen or methyl.

4. Compounds of the formula I according to claim 1, characterised in that $R^1$ represents methyl and $R^2$ represents hydrogen.

5. Compounds of the formula I according to claim 1, characterised in that R denotes pyrrolyl, indolyl, 5-amino-1,3-dimethyl-pyrazolyl, 5-hydroxy-3-methyl-1-phenyl-pyrazolyl or 1,4-dihydro-2-oxo-benz(d)(1,3)-oxazinyl.

6. Compounds of the formula I according to claim 1, characterised in that R is a phenyl radical substituted by $R^3$ and $R^4$.

7. Compounds of the formula I according to claim 1, characterised in that $R^4$ denotes hydrogen, ($C_1$-$C_4$)alkyl or ($C_1$-$C_4$)alkoxy.

8. Compounds of the formula I according to claim 1, characterised in that $R^4$ denotes hydrogen.

9. Compounds of the formula I according to claim 1, characterised in that $R^3$ denotes 2-methoxy-ethoxy, 3-pyridyl-methoxy, aminocarbonyl-methoxy, hydroxycarbonyl-methoxy, methylthio, (2-methoxy-ethyl)-amino-carbonyl-methoxy, 3-pyridyl-methyl, 5-methyl-1,3,4-oxadiazol-2-yl, 2-hydroxy-4-methyl-pyrid-6-yl-methoxy, 2-(imidazol-1-yl)-ethoxy, (2-oxo-oxazolidin-5-yl)methoxy, 2-(methoxycarbonyl-pyrrolidin-1-yl)-ethoxy, 2-oxo-pyrrolidin-1-yl, 2,5-dioxopyrrolidin-1-yl, 2-oxo-imidazlidin-1-yl, 3-oxo-pyrazolidin-1-yl, 2,4-dioxo-imidazolidin-1-yl, 2-oxo-oxazolidin-3-yl or thiazolidin-4-yl-carbonylamino.

10. Compounds of the formula I according to claim 1, characterised in that R denotes a phenyl radical substituted in the 4-position by $R^3$.

11. Compounds of the formula I according to claim 1, characterised in that $R^1$ denotes methyl, $R^2$ denotes hydrogen, R denotes a radical of the formula

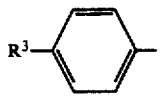

and $R^3$ denotes a radical of the formula

$R^{10}$—CO—NH— where $R^{10}$ denotes p-chlorophenoxymethyl, 2,4-dioxoimidazolidin-5-yl-methyl, 2,4-dioxo-imidazolidin-3-yl-methyl, 3-pyridyl-oxy-methyl, 3-pyridyl-methoxy-methyl, 4-pyridyl-thiomethyl, 4-pyridyl-sulphinyl-methyl, 4-pyridylsulphonyl-methyl, 2-oxo-thiazolidin-4-yl, 3-oxo-perhydro-1,4-thiazin-5-yl, 1-oxido-3-oxo-perhydro-1,4-thiazin-5-yl, 5-oxo-perhydro-1,4-thiazepin-3-yl, 1-oxido-5-oxo-perhydro-1,4-thiazepin-3-yl, 1,1-dioxido-5-oxo-perhydro-1,4-thiazepin-3-yl or a radical of the formula

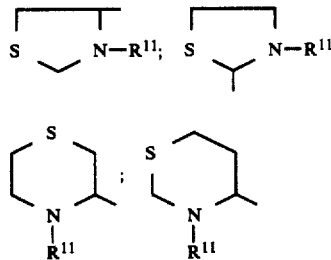

and their pharmacologically acceptable acid addition salts.

12. 4,5-Dihydro-3(2H)-pyridazinones according to claim 11, characterised in that $R^{11}$ denotes hydrogen, formyl, acetyl, tert.-butoxy-carbonyl or benzyloxycarbonyl.

13. Pharmaceutical formulation containing an effective dose of a substituted 4,5-dihydro-3(2H)-pyridazinone of the formula I of claim 1 or of a pharmacologically acceptable acid addition salt thereof, in addition to pharmacologically permitted excipients.

14. 6-(L-4-Thiazolidin-4-yl-carbonyl-amino-phenyl)-5-methyl-4,5-dihydro-3(2H)-pyridazinone.

15. Pharmaceutical formulation containing an effective dose of a substituted 4,5-dihydro-3(2H)-pyridazinone of the formula I of claim 3 or of a pharmacologically acceptable acid addition salt thereof, in addition to pharmacologically permitted excipients.

16. Pharmaceutical formulation containing an effective dose of a substituted 4,5-dihydro-3(2H)-pyridazione of the formula I of claim 8 or of a pharmacologically acceptable acid addition salt thereof, in addition to pharmacologically permitted excipients.

17. Pharmaceutical formulation containing an effective dose of a substituted 4,5-dihydro-3(2H)-pyridazinone of the formula I of claim 11 or of a pharmacologically acceptable acid addition salt thereof, in addition to pharmacologically permitted excipients.

18. A process for treating diseases of the heart and circulatory system which comprises administering an effective amount of a substituted 4,5-dihydro-3-(2H)-pyridazinone of the formula I of claim 1, or of a pharmacologically-acceptable acid addition salt thereof, to a host which is in need of such treatment.

19. A process for treating diseases of the heart and circulatory system which comprises administering an effective amount of a substituted 4,5-dihydro-3-(2H)-pyridazinone of the formula I of claim 3, or of a pharmacologically-acceptable acid addition salt thereof, to a host which is in need of such treatment.

20. A process for treating diseases of the heart and circulatory system which comprises administering an effective amount of a substituted 4,5-dihydro-3-(2H)-pyridazinone of the formula I of claim 8, or of a pharmacologically-acceptable acid addition salt thereof, to a host which is in need of such treatment.

21. A process for treating diseases of the heart and circulatory system which comprises administering an effective amont of a substituted 4,5-dihydro-3-(2H)-pyridazinone of the formula I of claim 11, or of a pharmacologically-acceptable acid addition salt thereof, to a host which is in need of such treatment.

* * * * *